US008114831B2

(12) United States Patent
Shailubhai et al.

(10) Patent No.: US 8,114,831 B2
(45) Date of Patent: Feb. 14, 2012

(54) GUANYLATE CYCLASE RECEPTOR AGONISTS FOR THE TREATMENT OF TISSUE INFLAMMATION AND CARCINOGENESIS

(75) Inventors: Kunwar Shailubhai, Audobon, PA (US); Gregory Nikiforovich, St. Louis, MO (US); Gary S. Jacob, New York, NY (US)

(73) Assignee: Synergy Pharmaceuticals Inc., New York, NY (US)

( * ) Notice: Subject to any disclaimer, the term of this patent is extended or adjusted under 35 U.S.C. 154(b) by 0 days.

(21) Appl. No.: 12/763,707

(22) Filed: Apr. 20, 2010

(65) Prior Publication Data

US 2011/0212884 A1 Sep. 1, 2011

Related U.S. Application Data

(63) Continuation of application No. 11/347,115, filed on Feb. 2, 2006, now Pat. No. 7,799,897, which is a continuation of application No. 10/107,814, filed on Mar. 28, 2002, now Pat. No. 7,041,786.

(60) Provisional application No. 60/279,438, filed on Mar. 29, 2001, provisional application No. 60/279,437, filed on Mar. 29, 2001, provisional application No. 60/300,850, filed on Jun. 27, 2001, provisional application No. 60/303,806, filed on Jul. 10, 2001, provisional application No. 60/307,358, filed on Jul. 25, 2001, provisional application No. 60/348,646, filed on Jan. 17, 2002.

(51) Int. Cl.
*A61K 38/10* (2006.01)
*A61K 38/12* (2006.01)

(52) U.S. Cl. ....... 514/1.1; 514/12.2; 514/15.1; 530/317; 530/321; 530/326

(58) Field of Classification Search .................. 514/1.1, 514/12.2, 15.1; 530/317, 321, 326
See application file for complete search history.

(56) References Cited

U.S. PATENT DOCUMENTS

| | | | |
|---|---|---|---|
| 5,489,670 | A | 2/1996 | Currie et al. |
| 5,518,888 | A | 5/1996 | Waldman |
| 5,578,709 | A | 11/1996 | Woiszwillo |
| 5,601,990 | A | 2/1997 | Waldman |
| 5,731,159 | A | 3/1998 | Waldman |
| 5,879,656 | A | 3/1999 | Waldman |
| 5,928,873 | A | 7/1999 | Waldman |
| 5,969,097 | A | 10/1999 | Wiegand et al. |
| 6,060,037 | A | 5/2000 | Waldman |
| 6,235,782 | B1 | 5/2001 | Pamukcu et al. |
| 7,041,786 | B2 | 5/2006 | Shailubhai et al. |
| 2002/0078683 | A1 | 6/2002 | Katayama et al. |
| 2002/0128176 | A1 | 9/2002 | Forssmann et al. |
| 2003/0073628 | A1 | 4/2003 | Shailubhai et al. |
| 2005/0016244 | A1 | 1/2005 | Hergemoller |
| 2005/0032684 | A1 | 2/2005 | Cetin et al. |
| 2006/0086653 | A1 | 4/2006 | St. Germain |
| 2007/0101158 | A1 | 5/2007 | Elliott |
| 2008/0137318 | A1 | 6/2008 | Rangaraj et al. |
| 2008/0151257 | A1 | 6/2008 | Yasuda et al. |

FOREIGN PATENT DOCUMENTS

| | | | |
|---|---|---|---|
| WO | WO-0125266 | A1 | 4/2001 |
| WO | WO-02062369 | A2 | 8/2002 |
| WO | WO-02078683 | A1 | 10/2002 |
| WO | WO-02098912 | A2 | 12/2002 |
| WO | WO-2005016244 | A2 | 2/2005 |
| WO | WO-2006086653 | A2 | 8/2006 |
| WO | WO-2007022531 | A2 | 2/2007 |
| WO | WO-2007101158 | A2 | 9/2007 |
| WO | WO-2008137318 | A1 | 11/2008 |
| WO | WO-2008151257 | A2 | 12/2008 |
| WO | WO-2009149278 | A1 | 12/2009 |
| WO | WO-2009149279 | A2 | 12/2009 |

OTHER PUBLICATIONS

Rolfe et al. (Clin Sci (Lond). Feb. 1999; 96 (2): 165-70).*
Askling et al., "Colorectal Cancer Rates Among First Degree Realatives of Patients with Inflammatory Bowel Disease: A Population-Based Cohort Study", *Lancet*, 357:262-266, 2001.
Barbara et al., "A role for inflammation in irritable bowel syndrome", *Gut.*, 51(Suppl. 1):141-144 (2002).
Basoglu et al., In: Proceedings of the Second FEPS Congress, Jun. 29-Jul. 4, 1999, Prague, Czech Republic, lf2.cuni.cz/physiolres/feps/basoglu.htm.
Baxter et al., "Natriuretic peptides and myocardial ischaemia", *Basic Res. Cardiol.*, 99(2):71-75 (2004).
Beltowski "Guanylin and Related Peptides" *J Physiol. Pharmacol.*, 52(3):351, 2001.
Bergers et al., "Extrinsic regulators of epithelial tumor progression: metalloproteinases", *Curr. Opin. Gen. Dev.*, 10:120-127 (2000).

(Continued)

*Primary Examiner* — Stephen Rawlings
(74) *Attorney, Agent, or Firm* — Mintz Levin Cohn Ferris Glovsky and Popeo, P.C.; Ivor R. Elrifi, Ph.D.; Cynthia A. Kozakiewicz, J.D., Ph.D.

(57) ABSTRACT

A method of treatment of inflamed, pre-cancerous or cancerous tissue or polyps in a mammalian subject is disclosed. The treatment involves administration of a composition of at least one peptide agonist of a guanylate cyclase receptor and/or other small molecules that enhance intracellular production of cGMP. The at least one peptide agonist of a guanylate cyclase receptor may be administered either alone or in combination with an inhibitor of cGMP-dependent phosphodiesterase. The inhibitor may be a small molecule, peptide, protein or other compound that inhibits the degradation of cGMP. Without requiring a particular mechanism of action, this treatment may restore a healthy balance between proliferation and apoptosis in the subject's population of epithelial cells, and also suppress carcinogenesis. Thus, the method may be used to treat, inter alia, inflammation, including gastrointestinal inflammatory disorders, general organ inflammation and asthma, and carcinogenesis of the lung, gastrointestinal tract, bladder, testis, prostate and pancreas, or polyps.

4 Claims, No Drawings

OTHER PUBLICATIONS

Bhakdi et al., "Release of interleukin-1 beta associated with potent cytocidal action of staphylococcal alpha-toxin on human monocytes", *Infect. Immun.*, 57(11):3512-3519 (1989).

Brown et al., "A Receptor-Medicated Pathway for Cholesterol Homeostasis", *Sci.*, 232:34-47 (1986).

Burnham, N.L., "Polymers for delivering peptides and proteins", *Am. J. Hosp. Pharm.*, 51:210-218 (1994).

Caliceti et al., "Synthesis and biopharmaceutical characterisation of new poly(hydroxyethylaspartamide) copolymers as drug carriers", *Biochimica et Biophysica Acta*, 1528:177-186 (2001).

Camilleri et al., "Management of the irritable bowel syndrome", *Gastroenterol.*, 120:652-668 (2001).

Carrithers et al., "Guanylyl cyclase C is a selective marker for metastatic colorectal tumors in human extraintestinal tissues", *Proc. Natl. Acad. Sci. USA*, 93:14827-14832 (1996).

Cermak et al., "Natriuretic peptides increase a K+ conductance in rat mesangial cells", *Pflügers Arch.-Eur. J. Physiol.*, 431:571-577 (1996).

Cheng et al., "Defective intracellular transport and processing of CFTR is the molecular basis of most cystic fibrosis", *Cell*, 63:827-834 (1990).

Chino et al., "Topological isomers of human uroguanylin: interconversion between biologically active and inactive isomers", *FEBS Letters*, 421:27-31 (1998).

Cohen et al., "Guanylin mRNA expression in human intestine and colorectal adenocarcinoma", *Lab. Invest.*, 78:101-108 (1998).

Collins, SM., "The Relationship of Enteric Microbial Infection and Functional Bowel Disorders", *J. Clin. Gastroenterol*, 41 Suppl. 1:S30-32 (2007).

Cui et al., "The Permissive Effect of Zinc Deficiency on Uroguanylin and Inducible Nitric Oxide Synthase Gene Upregulation in Rat Intestine Induced by Interleukin 1a is Rapidly Reversed by Zinc Repletion", *J. Nutri..*, 133(1): 51-56 (2003).

Currie et al., "Guanylin: an endogenous activator of intestinal guanylate cyclase", *Proc. Natl. Acad. Sci. USA*, 89:947-951 (1992).

Database BIOSIS (Online), Biosciences Information Service, Philadelphia, PA, U.S., Apr. 2006, Refaat et al., "Sp304, an analog of uroguanylin, ameliorates inflammation in a model of experimental colitis", XP002540570, Database Accession No. PREV200600503788.

De Luca et al., "Inflammation and Insulin Resistance", FEBS Letter, 582:97-105 (2008).

De Sauvage et al., "Precursor structure, expression, and tissue distribution of human guanylin", *Proc. Natl. Acad. Sci. USA*, 89:9089-9093 (1992).

Delvaux et al., "Effect of alosetron on responses to colonic distension in patients with irritable bowel syndrome ", *Aliment Pharmacol. Ther.*, 12:849-855 (1998).

Dennis et al. "Off by a whisker", *Nature*, 442:739-741 (2006).

Deschner et al., "Proliferative defects in ulcerative colitis patients", *Can. Invest.*, 1:41-47 (1983).

Dunfield et al., "Energy parameters in polypeptides. 8. Empirical potential energy algorithm for the conformational analysis of large molecules", J. *Phys. Chem.*, 82:2609-2616 (1978).

Eastwood, G. "Epithelial Renewal in Premalignant Conditions of the Gastrointestinal Tract: A Review", *J. Clin. Gastroenterol.*, 14(1):S29-S33 (1992).

Ettorre et al., "Mucosal changes in ileal pouches after restorative proctocolectomy for ulcerative and Crohn's colitis", *Dis. Colon Rectum*, 43:1743-1748 (2000).

Evan et al., "Proliferation, cell cycle and apoptosis in cancer", *Nature* (London), 411:342-348 (2001).

Forte, L.R., "Guanylin regulatory peptides: Structures, biological activities mediated by cyclic GMP and pathobiology", *Reg. Pep.*, 81(1-3):25-39 (1999).

Gali et al., "In Vivo Evaluation of an $^{111}$In -labeled ST-peptide Analog for Specific-Targeting of Human Colon Cancers" *Nuclear Medicine and Biology*, 28(8):903-909 (2001).

Garcia et al., "Processing and characterization of human proguanylin expressed in *Escherichia coli*", *J. Biol. Chem.*, 268(30):22397-22401 (1993).

Greenberg et al., "Comparison of effects of uroguanylin, guanylin, and *Escherichia coli* heat-stable enterotoxin STa in mouse intestine and kidney: evidence that uroguanylin is an intestinal natriuretic hormone", *J. Invest. Med.*, 45(5):276-282 (1997).

Guba et al., "Guanylin strongly stimulates rat duodenal HCO3-secretion: proposed mechanism and comparison with other secretagogues", *Gastroenterol.*, 111(6):1558-1568 (1996).

Gülcan et al., "Increased Frequency of Prediabetes in Patients With Irritable Bowel Syndrome", *Am. J. Med. Sci.*, 338:116-119 (2009).

Gülcan et al., "The Predictive Value of CRP Levels on Future Severe Renal Disease in Overweight and Obese Subjects Without Diabetes Mellitus and Hypertension", *Am. J. Med. Sci.*, 334:444-451 (2007).

Gura, T., "Systems for identifying new drugs are often faulty ", *Sci.*, 278:1041-1042 (1997).

Hamman et al., "Oral delivery of peptide drugs", *BIODRUGS*, 19(3):165-177 (2005).

Hamra et al., "Uroguanylin: structure and activity of a second endogenous peptide that stimulates intestinal guanylate cyclase", *Proc. Natl. Acad. Sci. USA*, 90:10464-10468 (1993).

Harris et al., "Drug evaluation: linaclotide, a new direction in the treatment of irritable bowel syndrome and chronic constipation", *Curr. Opin. Mol. Ther.*, 9(4):403-410 (2007).

Hidaka et al., "Dual Function of the Propeptide of Prouroguanylin in the Folding of the Mature Peptide: Disulfide-Coupled Folding and Dimerization", *J. Biol. Chem.*, 33:25155-25162 (2000).

Hidaka et al., "In Vitro Disulfide-Coupled Folding of Guanylyl Cyclase-Activating Peptide and Its Precursor Protein ", *Biochem.*, 37:8498-8507 (1998).

Hill et al., "A new human guanylate cyclase-activating peptide (GCAP-II, uroguanylin): precursor cDNA and colonic expression", Biochemica Biophysica Acta, 12(53):146-149 (1995).

Hill et al., "Analysis of the human guanylin gene and the processing and cellular localization of the peptide", *Proc. Natl. Acad. Sci. USA*, 92:2046-2050 (1995).

Hinds et al., "Synthesis and Characterization of Poly(ethylene glycol)-Insulin Conjugates <http://pubs.acs.org/doi/abs/10.1021/bc9901189>", *Bioconjug. Chem.*, 11:195-201 (2000).

Hudson et al., "Rethinking cystic fibrosis pathology: the critical role of abnormal reduced glutathione (GSH) transport caused by CFTR mutation", *Free Rad. Biol. Med.*, 30:1440-1461 (2001).

Hughes et al., "Intracellular $K^+$ Suppresses the Activation of Apoptosis in Lymphocytes", *J. Biol. Chem.*, 272(48):30567-30576 (1997).

Joo et al., "Regulation of intestinal Cl- and HCO3-secretion by uroguanylin", *Am. J. Physiol.*, 274:G633-G644 (1998).

Kelland L.R., "Of mice and men": values and liabilities of the athymic nude mouse model in anticancer drug development, *Eur. J. Can.*, 40:827-836 (2004).

Klodt et al., "Synthesis, biological activity and isomerism of guanylate cyclase C-activating peptides guanylin and uroguanylin", *J. Pep. Res.*, 50(2):77-152 (1997).

Leister et al., "Human Colorectal Cancer: High Frequency of Deletions at Chromosome 1p35", *Can. Res.*, 50:7232-7235 (1990).

Lipkin, M., "Gastric cell regeneration", *Arch. Fr. Mal. Appl. Dig.* (Paris), 61(10-11):691-693 (1972).

Lorenz et al., "Uroguanylin knockout mice have increased blood pressure and impaired natriuretic response to enteral NaCl load", *J. Clin. Invest.*, 112(8):1244-1254 (2003).

Mahato et al., "Emerging trends in oral delivery of peptide and protein drugs", *Crit. Rev. Ther. Drug Carrier Systems*, 20(2-3):153-214 (2003).

Miyazato et al., "Cloning and Characterization of a cDNA Encoding a Precursor for Human Uroguanylin", *Biochem. Biophys. Res. Comm.*, 219:644-648 (1996).

Moon et al., "Effects of age, ambient temperature, and heat-stable *Escherichia coli* enterotoxin on intestinal transit in infant mice", *Infect. Immun.*, 25(1):127-132 (1979).

Müller-Lissner et al., "Safety, Tolerability, and Efficacy of Tegaserod over 13 Months in Patients with Chronic Constipation", *Am. J. Gastroenterol.*, 101:2558-2569 (2006).

Nathan et al., "Copolymers of lysine and polyethylene glycol: a new family of functionalized drug carriers <http://pubs.acs.org/doi/abs/10.1021/bc00019a008>", *Bioconjug. Chem.*, 4(1):54-62 (1993).

Nemethy et al., "Energy parameters in polypeptides. 9. Updating of geometrical parameters, non-bonded interactions, and hydrogen bond interactions for the naturally occurring amino acids", *J. Phys. Chem.*, 87:1883-1887 (1983).
Nikiforovich et al., "Topographical requirements for -selective opioid peptides", Biopolymers, 31:941-955 (1991).
Nikiforovich, G., "Computational molecular modeling in peptide design", *Int. J. Pep. Prot. Res.*, 44:513-531 (1994).
Nyburg et al., "Some uses of best molecular fit routine Acta", Crystallographica B30 (Part I):251-253 (1974).
Ohbayashi et al., "Effects of Uroguanylin and Guanylin Against Antigen-Induced Bronchoconstriction and Airway Microvascular Leakage in Sensitized Guinea-Pigs", *Life Sci.*, 62(20): 1833-1844 (1998).
Peterson et al., "Integrating pharmacology and in vivo cancer models in preclinical drug development", *Eur. J. Can.*, 40:837-844 (2004).
Pitari et al., "Guanylyl cyclase C agonists regulate progression through the cell cycle of human colon carcinoma cells", *Proc. Natl. Acad. Sci. USA*, 98(14):7846-7851 (2001).
Potten et al., "Regulation and Significance of Apoptosis in the Stem Cells of the Gastrointestinal Epithelium", *Stem Cells*, 15:82-93 (1997).
Provenzale et al., "Surveillance Issues in Inflammatory Bowel Disease: Ulcerative Colitis", *J Clin. Gastroenterol*, 32:99-105 (2001).
Ramamoorthy et al., "Phosphorylation of Threonine Residue 276 Is Required for Acute Regulation of Serotonin Transporter by Cyclic GMP", *J. Biol. Chem.*, 282(16):11639-11647 (2007).
Samuel et al., "Absorption of bile acids from the large bowel in man", *J Clin. Invest.*, 47:2070-2078 (1968).
Schulz et al., "Guanylyl cyclase is a heat-stable enterotoxin receptor", *Cell*, 63(5):941-948 (1990).
Schulz et al., "Side chain contributions to the interconversion of the topological isomers of guanylin-like peptides", *J. Pep. Sci.*, 11:319-330 (2005).
Sciaky et al., "-Mapping of guanylin to murine chromosome 4 and human chromosome 1p34p35", *Genomics*, 26:427-429 (1995).
Sellers et al., "Heat-stable enterotoxin of *Escherichia coli* stimulates a non-CFTR-mediated duodenal bicarbonate secretory pathway", *Am. J. Physiol. Gastrointest. Liver Physiol.*, 288:G654-G663 (2005).
Shailubhai et al., Guanilib, an agonist of Guanylate C, is a newclass of oral drug candidate for GI disorders and colon cancer, [abstract]: In GTCbio, 2008.
Shailubhai et al., "Guanilib, an antagonist of Guanylate C, is a new class of oral drug candidate that amerliorates inflammation in models of experimental colitis", [Abstract] : In Crohn's and Colitis Foundation of America, 2007.
Shailubhai et al., "SP-304 to Treat GI Disorders—Effects of a Single, Oral Dose of SP-304 in Safety, Tolerability, Pharmaokinetics and Pharmacodynamics in Healthy Volunteers", [Abstract]; In Digestive Disease Week, 2009.
Shailubhai et al., "Uroguanylin Treatment Suppresses Polyp Formation in the Apc Min/+ Mouse and Induces Apoptosis in Human Colon Adenocarcinoma Cells in via Cyclic GMP", *Can. Res.*, 60:5151-5157 (2000).
Shailubhai et al., *Clin. Cancer Res.*, (Proc. 1999 AACR NCI EORTC Int. Conf.), [Abstract], 5(Suppl.), 1999.
Shailubhai, K., "Therapeutic applications of guanylate cyclase-C receptor agonists", *Curr. Opin. Drug Discov. Dev.*, 5(2):261-268 (2002).
Shinozaki et al., "High proliferative activity is associated with dysplasia in ulcerative colitis", *Dis. Colon Rectum*, 43:S34-S39 (2000).
Sindice et al., "Guanylin, Uroguanylin, and Heat-stable Euterotoxin Activate Guanylate Cyclase C and/or a Pertussis Toxin-sensitive G Protein in Human Proximal Tubule Cells", *J. Biol. Chem.*, 277:17758-17764 (2002).
Spranger et al., "Inflammatory Cytokines and the Risk to Develop Type 2 Diabetes: Results of the Prospective Population-Based European Prospective Investigation into Cancer and Nutrition (EPIC)-Potsdam Study", *Diabetes*, 52:812-817 (2003).
Takada et al., "Alteration of a Single Amino Acid in Peroxisome Proliferator-Activated Receptor-(PPAR ) Generates a PPAR Phenotype", Mol. Endocrinol., 14(5):733-740 (2000).
Talley et al., "Medical costs in community subjects with irritable bowel syndrome", *Gastroenterol.*, 109:1736-1741 (1995).
Tian et al: "STa Peptide Analogs for Probing Guanylyl Cyclase C" *BIOPOLYMERS* (*Pept. Sci.*), 90(5):713, 2008.
Tilg et al., "Inflammatory Mechanisms in the Regulation of Insulin Resistance", *Mol. Med.*, 14:222-231 (2008).
Vaandrager, A.B., "Structure and Function of the Heat Stable Enterotoxin Receptor/Guanylyl Cyclase C", *Mol. Cell. Biochem.*, 230:73-83 (2002).
Venkatakrishnan et al., "Exaggerated Activation of Nuclear Factor-B and Altered I B-Processing in Cystic Fibrosis Bronchial Epithelial Cells", Am. J. Resp. Cell Mol. Biol., 23(3):396-403 (2000).
Veronese F.M., "Peptide and protein PEGylation: a review of problems and solutions", *Biomaterials*, 22:405-417 (2001).
Weber et al., Activation of NF-B in airway epithelial cells is dependent on CFTR trafficking and CI channel function, Am. J. Physiol. Lung Cell Mol. Biol., 281(1):L71-78 (2001).
Welsh et al., "Molecular mechanisms of CFTR chloride channel dysfunction in cystic fibrosis", DL*Cell*, 73:1251-1254 (1993).
Whitaker et al., "The Uroguanylin Gene (*Guca1b*) Is Linked to Guanylin (*Guca2*) on Mouse ChromDNosome 4", *Genomics*, 45:348-354 (1997).
Wong et al., "Histogenesis of human colorectal adenomas and hyperplastic polyps: the role of cell proliferation and crypt fission", *Gut.*, 50:212-217 (2002).
Wong et al., "Cell proliferation in gastrointestinal mucosa", *J. Clin. Pthol.*, 52:321-33 (1999).
Wu et al., "Atrial Natriuretic Peptide Induces Apoptosis in Neonatal Rat Cardiac Myocytes", *J. Biol. Chem.*, 272(23):14860-14866 (1997).
Zhang et al., "Gene Expression Profiles in Normal and Cancer Cells", *Sci.* 276:1268-1272 (1997).
Zimmerman et al., "Influence of local interactions on protein structure. I. Conformational energy studies of N-acetyl-N -methylamides of pro-X and X-pro dipeptides", Biopolymers, 16:811-843 (1977).
Bakre et al., "Expression and Regulation of the cGMP-Binding, cGMP-Specific Phosphodiesterase (PDE5) in Human Colonic Epithelial Cells: Role in the Induction of Cellular Refractoriness to the Heat-stable Enterotoxin Peptide", *J. Cell. Biol.*, 77:159-167 (2000).
Duncan, Ruth, "Drug-polymer COnjugates: Potential for Imporved Chemotherapy", *Anti-Can. Drugs*, 3:175-210 (1992).
Fan et al., "Structure and Activity of Uroguanylin and Guanylin from the Intestine and Urine of Rats", *Am. J. Physiol. Endocrinol. Metab.*, 273:957-964 (1997).
Fonteles, et al., "Natriuretic and Kaliuretic Activities of Guanylin and Uroguanylin in Isolated Perfused Rat Kidney", *Am. J. Physiol. Renal Physiol.*, 275:191-197 (1998).
Genbank 1UYBA—Chain A, Solution Structure B—Form Uroguanylin, Mar. 15, 2010.
Genbank AAC50416.1; GUCA2B (human, 1994), Mar. 11, 2010.
Genbank IUYAA—Chain A, Solution Structure A-Form Uroguanylin, Mar. 15, 2010.
GenBank: AAB18760.1 (rat, 1995), Mar. 11, 2010.
GenBank: AAB30324.1; GUCA2B (human, 1994), Mar. 11, 2010.
GenBank: AAD09215.1 (mouse, 1996), Mar. 11, 2010.
GenBank: CAA98994.1 (guinea pig, 1996), Mar. 11, 2010.
GenBank: CAB06042.1 (pig, 1996), Mar. 11, 2010.
Genbank: PRF: 738946 (opossum, 1993), Mar. 15, 2010.
Kita et al., "Characterization of Human Uroguanylin: A Member of the Guanylin Peptide Family", *Am. J. Physiol.*, 266:F342-8 (1994).
Krause et al., "The Guanylin and Uroguanylin Peptide Hormones and Their Receptors", Acta Anat., 160:213-231 (1997).
Lam et al., "Serotonin and energy balance: molecular mechanisms and implications for type 2 diabetes", *Expert Rev. Mol. Med.*, 9:1-24 (2007).
Li et al., "Purification, cDNA Sequence and Tissue Distribution of Rat Uroguanylin", Reg. Pep., 68:45 -56 (1997).
Magert et al., "Porcine Guanylin and Uroguanylin: cDNA Sequences, Deduced Amino Acid Sequences, and Biological Activity of the Chemically Synthesized Peptides", Biochem. Biophys. Res. Comm., 259:141-148 (1999).

Marx et al., "One Peptide, Two Topologies: Structure and Interconversion Dynamics of Human Uroguanylin Isomers", J.Pep. Res., 52:229-240 (1998).
Miyazato et al., "Uroguanylin Gene Expression in the Alimentary Tract and Extra-Gastrointestinal Tissues", FEBS Letters, 398:170-174 (1996).
Nakazato et al., "Tissue Distribution, Cellular Source, and Structural Analysis of Rat Immunoreactive Uroguanylin", *Endocrinol.*, 139:5247-5254 (1998).
Perkins et al., "Uroguanylin is Expressed by Enterochromaffin Cells in the Rat Gastrointestinal Tract", *Gastroenterol.*, 113:1007-1014 (1997).
Remington, JP., *Remington's Pharmaceutical Sciences*, Mack Pub. Co., 16th edition (1980).
Veronese et al., "BioConjugation in Pharmaceutical Chemistry", *Farmaco*, 54:497-516 (1999).
Waldman et al., "Heterogeneity of Guanylyl Cyclase C Expressed by Human Colorectal Cancer Cell Lines in Vitro", *Can. Epidemiol., Biomarkers & Prevention*, 7:505-514 (1998).
Whitaker et al., "The Uroguanylin Gene (*Guca1b*) Is Linked to Guanylin (*Guca2*) on Mouse Chromosome 4", *Genomics*, 45:348-354 (1997).
Response to European Patent Office Communication dated Mar. 16, 2007 for European Application No. 02721604.3.
European Patent Office Communication dated Aug. 12, 2008.
CombiMab, Inc. Annex to Notice of Opposition aginst European Patent 1,379,224 B1, Apr. 22, 2010.
Summons to Attend Oral hearing dated Jun. 6, 2011 for European Patent Application No. 02721604.
Response to Communication from Opposition Division relating to European Patent No. 1379224, Oct. 8, 2010.
Shailubhai et al., "Guanylin Peptides: New Class of Oral Drug Candidates", [Abstract]: In World Congress, 2008.
Shailubhai et al., "Guanylate Cyclase-C Agonists as a New Class of Drug Candidates for GI Motility and Inflammatory Bowel Disease", [Abstract], 2009.

* cited by examiner

SEQUENCE LISTING

```
<160> NUMBER OF SEQ ID NOS: 23

<210> SEQ ID NO 1
<211> LENGTH: 16
<212> TYPE: PRT
<213> ORGANISM: Homo sapiens
<220> FEATURE:
<221> NAME/KEY: DISULFID
<222> LOCATION: (4)..(12)
<220> FEATURE:
<221> NAME/KEY: DISULFID
<222> LOCATION: (7)..(15)

<400> SEQUENCE: 1

Asn Asp Asp Cys Glu Leu Cys Val Asn Val Ala Cys Thr Gly Cys Leu
1               5                   10                  15


<210> SEQ ID NO 2
<211> LENGTH: 16
<212> TYPE: PRT
<213> ORGANISM: Artificial Sequence
<220> FEATURE:
<223> OTHER INFORMATION: Chemically synthesized peptide
<220> FEATURE:
<221> NAME/KEY: VARIANT
<222> LOCATION: (2)..(2)
<223> OTHER INFORMATION: wherein Xaa is a Glu or an Asp
<220> FEATURE:
<221> NAME/KEY: VARIANT
<222> LOCATION: (3)..(3)
<223> OTHER INFORMATION: wherein Xaa is a Glu or an Asp
<220> FEATURE:
<221> NAME/KEY: DISULFID
<222> LOCATION: (4)..(12)
<220> FEATURE:
<221> NAME/KEY: DISULFID
<222> LOCATION: (7)..(15)
<220> FEATURE:
<221> NAME/KEY: VARIANT
<222> LOCATION: (10)..(10)
<223> OTHER INFORMATION: wherein Xaa is a Val or an Ala
<220> FEATURE:
<221> NAME/KEY: VARIANT
<222> LOCATION: (11)..(11)
<223> OTHER INFORMATION: wherein Xaa is an Ala or an Aib
<220> FEATURE:
<221> NAME/KEY: VARIANT
<222> LOCATION: (14)..(14)
<223> OTHER INFORMATION: wherein Xaa is a Gly or an Ala

<400> SEQUENCE: 2

Asn Xaa Xaa Cys Glu Leu Cys Val Asn Xaa Xaa Cys Thr Xaa Cys Leu
1               5                   10                  15
```

<210> SEQ ID NO 3
<211> LENGTH: 16
<212> TYPE: PRT
<213> ORGANISM: Artificial Sequence
<220> FEATURE:
<223> OTHER INFORMATION: Chemically synthesized peptide
<220> FEATURE:
<221> NAME/KEY: VARIANT
<222> LOCATION: (2)..(2)
<223> OTHER INFORMATION: wherein Xaa is a Glu or an Asp
<220> FEATURE:
<221> NAME/KEY: VARIANT
<222> LOCATION: (3)..(3)
<223> OTHER INFORMATION: wherein Xaa is a Glu or an Asp
<220> FEATURE:
<221> NAME/KEY: DISULFID
<222> LOCATION: (4)..(12)
<220> FEATURE:
<221> NAME/KEY: MISC_FEATURE
<222> LOCATION: (7)..(7)
<223> OTHER INFORMATION: The amino acid at position 7 is Mpt
(mercaptoproline)
<220> FEATURE:
<221> NAME/KEY: DISULFID
<222> LOCATION: (7)..(15)
<220> FEATURE:
<221> NAME/KEY: VARIANT
<222> LOCATION: (10)..(10)
<223> OTHER INFORMATION: wherein Xaa is a Val or a Pro
<220> FEATURE:
<221> NAME/KEY: VARIANT
<222> LOCATION: (11)..(11)
<223> OTHER INFORMATION: wherein Xaa is an Ala or an Aib
<220> FEATURE:
<221> NAME/KEY: VARIANT
<222> LOCATION: (14)..(14)
<223> OTHER INFORMATION: wherein Xaa is a Gly or an Ala

<400> SEQUENCE: 3

Asn Xaa Xaa Cys Glu Leu Xaa Val Asn Xaa Xaa Cys Thr Xaa Cys Leu
1 5 10 15

<210> SEQ ID NO 4
<211> LENGTH: 16
<212> TYPE: PRT
<213> ORGANISM: Artificial Sequence
<220> FEATURE:
<223> OTHER INFORMATION: Chemically synthesized peptide
<220> FEATURE:
<221> NAME/KEY: VARIANT
<222> LOCATION: (2)..(2)
<223> OTHER INFORMATION: wherein Xaa is an Asp or a Glu
<220> FEATURE:
<221> NAME/KEY: VARIANT
<222> LOCATION: (3)..(3)
<223> OTHER INFORMATION: wherein Xaa is an Asp or a Glu
<220> FEATURE:
<221> NAME/KEY: DISULFID
<222> LOCATION: (4)..(12)
<220> FEATURE:
<221> NAME/KEY: VARIANT
<222> LOCATION: (4)..(4)
<223> OTHER INFORMATION: wherein Xaa is a Cys or a Pen
<220> FEATURE:
<221> NAME/KEY: VARIANT
<222> LOCATION: (7)..(7)
<223> OTHER INFORMATION: wherein Xaa is a Cys or a Pen
<220> FEATURE:
<221> NAME/KEY: DISULFID
<222> LOCATION: (7)..(15)
<220> FEATURE:
<221> NAME/KEY: VARIANT
<222> LOCATION: (10)..(10)
<223> OTHER INFORMATION: wherein Xaa is a Val or a Pro
<220> FEATURE:
<221> NAME/KEY: VARIANT
<222> LOCATION: (11)..(11)
<223> OTHER INFORMATION: wherein Xaa is an Ala or an Aib
<220> FEATURE:
<221> NAME/KEY: VARIANT
<222> LOCATION: (12)..(12)
<223> OTHER INFORMATION: wherein Xaa is a Cys or a Pen
<220> FEATURE:
<221> NAME/KEY: VARIANT
<222> LOCATION: (14)..(14)
<223> OTHER INFORMATION: wherein Xaa is an Ala or a Gly
<220> FEATURE:
<221> NAME/KEY: VARIANT
<222> LOCATION: (15)..(15)
<223> OTHER INFORMATION: wherein Xaa is a Cys or a Pen

<400> SEQUENCE: 4

```
Asn Xaa Xaa Xaa Glu Leu Xaa Val Asn Xaa Xaa Xaa Thr Xaa Xaa Leu
1               5                   10                  15
```

<210> SEQ ID NO 5
<211> LENGTH: 16
<212> TYPE: PRT
<213> ORGANISM: Artificial Sequence
<220> FEATURE:
<223> OTHER INFORMATION: Chemically synthesized peptide
<220> FEATURE:
<221> NAME/KEY: VARIANT
<222> LOCATION: (2)..(2)
<223> OTHER INFORMATION: wherein Xaa is an Asp or a Glu
<220> FEATURE:
<221> NAME/KEY: VARIANT
<222> LOCATION: (3)..(3)
<223> OTHER INFORMATION: wherein Xaa is an Asp or a Glu
<220> FEATURE:
<221> NAME/KEY: DISULFID
<222> LOCATION: (4)..(12)
<220> FEATURE:
<221> NAME/KEY: VARIANT
<222> LOCATION: (4)..(4)
<223> OTHER INFORMATION: wherein Xaa is a Cys, a Pen, an Asp or a Glu
<220> FEATURE:
<221> NAME/KEY: VARIANT
<222> LOCATION: (7)..(7)
<223> OTHER INFORMATION: wherein Xaa is a Cys, a Dpr, a Pen, an Asp or a Glu
<220> FEATURE:
<221> NAME/KEY: DISULFID
<222> LOCATION: (7)..(15)
<220> FEATURE:
<221> NAME/KEY: VARIANT
<222> LOCATION: (10)..(10)
<223> OTHER INFORMATION: wherein Xaa is a Val or a Pro
<220> FEATURE:
<221> NAME/KEY: VARIANT
<222> LOCATION: (11)..(11)
<223> OTHER INFORMATION: wherein Xaa is an Ala or an Aib
<220> FEATURE:
<221> NAME/KEY: VARIANT
<222> LOCATION: (12)..(12)
<223> OTHER INFORMATION: wherein Xaa is a Cys, a Dpr or a Pen
<220> FEATURE:
<221> NAME/KEY: VARIANT
<222> LOCATION: (14)..(14)
<223> OTHER INFORMATION: wherein Xaa is a Gly or an Ala
<220> FEATURE:
<221> NAME/KEY: VARIANT
<222> LOCATION: (15)..(15)
<223> OTHER INFORMATION: wherein Xaa is a Cys, a Dpr, a Pen, an Asp or a Glu

<400> SEQUENCE: 5

```
Asn Xaa Xaa Xaa Glu Leu Xaa Val Asn Xaa Xaa Xaa Thr Xaa Xaa Leu
1               5                   10                  15
```

<210> SEQ ID NO 6
<211> LENGTH: 16

-continued

<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (1)..(1)
<223> OTHER INFORMATION: Xaa can be any naturally occurring amino acid
<220> FEATURE:
<221> NAME/KEY: DISULFID
<222> LOCATION: (4)..(12)
<220> FEATURE:
<221> NAME/KEY: MISC_FEATURE
<222> LOCATION: (5)..(6)
<223> OTHER INFORMATION: Xaa can be any naturally occurring amino acid
<220> FEATURE:
<221> NAME/KEY: DISULFID
<222> LOCATION: (7)..(15)
<220> FEATURE:
<221> NAME/KEY: MISC_FEATURE
<222> LOCATION: (8)..(8)
<223> OTHER INFORMATION: Xaa can be any naturally occurring amino acid
<220> FEATURE:
<221> NAME/KEY: MISC_FEATURE
<222> LOCATION: (10)..(11)
<223> OTHER INFORMATION: Xaa can be any naturally occurring amino acid
<220> FEATURE:
<221> NAME/KEY: MISC_FEATURE
<222> LOCATION: (13)..(14)
<223> OTHER INFORMATION: Xaa can be any naturally occurring amino acid
<220> FEATURE:
<221> NAME/KEY: MISC_FEATURE
<222> LOCATION: (16)..(16)
<223> OTHER INFORMATION: Xaa can be any naturally occurring amino acid

<400> SEQUENCE: 6

Xaa Glu Glu Cys Xaa Xaa Cys Xaa Asn Xaa Xaa Cys Xaa Xaa Cys Xaa
1               5                   10                  15

<210> SEQ ID NO 7
<211> LENGTH: 16
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (1)..(1)
<223> OTHER INFORMATION: Xaa can be any naturally occurring amino acid
<220> FEATURE:
<221> NAME/KEY: DISULFID
<222> LOCATION: (4)..(12)
<220> FEATURE:
<221> NAME/KEY: MISC_FEATURE
<222> LOCATION: (5)..(6)
<223> OTHER INFORMATION: Xaa can be any naturally occurring amino acid
<220> FEATURE:
<221> NAME/KEY: DISULFID
<222> LOCATION: (7)..(15)
<220> FEATURE:
<221> NAME/KEY: MISC_FEATURE
<222> LOCATION: (8)..(8)
<223> OTHER INFORMATION: Xaa can be any naturally occurring amino acid
<220> FEATURE:
<221> NAME/KEY: MISC_FEATURE
<222> LOCATION: (10)..(11)
<223> OTHER INFORMATION: Xaa can be any naturally occurring amino acid
<220> FEATURE:
<221> NAME/KEY: MISC_FEATURE
<222> LOCATION: (13)..(14)
<223> OTHER INFORMATION: Xaa can be any naturally occurring amino acid
<220> FEATURE:
<221> NAME/KEY: MISC_FEATURE
<222> LOCATION: (16)..(16)
<223> OTHER INFORMATION: Xaa can be any naturally occurring amino acid

<400> SEQUENCE: 7

-continued

```
Xaa Glu Asp Cys Xaa Xaa Cys Xaa Asn Xaa Xaa Cys Xaa Xaa Cys Xaa
1               5                   10                  15


<210> SEQ ID NO 8
<211> LENGTH: 16
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (1)..(1)
<223> OTHER INFORMATION: Xaa can be any naturally occurring amino acid
<220> FEATURE:
<221> NAME/KEY: DISULFID
<222> LOCATION: (4)..(12)
<220> FEATURE:
<221> NAME/KEY: MISC_FEATURE
<222> LOCATION: (5)..(6)
<223> OTHER INFORMATION: Xaa can be any naturally occurring amino acid
<220> FEATURE:
<221> NAME/KEY: DISULFID
<222> LOCATION: (7)..(15)
<220> FEATURE:
<221> NAME/KEY: MISC_FEATURE
<222> LOCATION: (8)..(8)
<223> OTHER INFORMATION: Xaa can be any naturally occurring amino acid
<220> FEATURE:
<221> NAME/KEY: MISC_FEATURE
<222> LOCATION: (10)..(11)
<223> OTHER INFORMATION: Xaa can be any naturally occurring amino acid
<220> FEATURE:
<221> NAME/KEY: MISC_FEATURE
<222> LOCATION: (13)..(14)
<223> OTHER INFORMATION: Xaa can be any naturally occurring amino acid
<220> FEATURE:
<221> NAME/KEY: MISC_FEATURE
<222> LOCATION: (16)..(16)
<223> OTHER INFORMATION: Xaa can be any naturally occurring amino acid

<400> SEQUENCE: 8

Xaa Asp Glu Cys Xaa Xaa Cys Xaa Asn Xaa Xaa Cys Xaa Xaa Cys Xaa
1               5                   10                  15


<210> SEQ ID NO 9
<211> LENGTH: 16
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (1)..(1)
<223> OTHER INFORMATION: Xaa can be any naturally occurring amino acid
<220> FEATURE:
<221> NAME/KEY: DISULFID
<222> LOCATION: (4)..(12)
<220> FEATURE:
<221> NAME/KEY: MISC_FEATURE
<222> LOCATION: (5)..(6)
<223> OTHER INFORMATION: Xaa can be any naturally occurring amino acid
<220> FEATURE:
<221> NAME/KEY: DISULFID
<222> LOCATION: (7)..(15)
<220> FEATURE:
<221> NAME/KEY: MISC_FEATURE
<222> LOCATION: (8)..(8)
<223> OTHER INFORMATION: Xaa can be any naturally occurring amino acid
<220> FEATURE:
<221> NAME/KEY: MISC_FEATURE
<222> LOCATION: (10)..(11)
<223> OTHER INFORMATION: Xaa can be any naturally occurring amino acid
<220> FEATURE:
<221> NAME/KEY: MISC_FEATURE
<222> LOCATION: (13)..(14)
<223> OTHER INFORMATION: Xaa can be any naturally occurring amino acid
<220> FEATURE:
```

<221> NAME/KEY: MISC_FEATURE
<222> LOCATION: (16)..(16)
<223> OTHER INFORMATION: Xaa can be any naturally occurring amino acid

<400> SEQUENCE: 9

Xaa Asp Asp Cys Xaa Xaa Cys Xaa Tyr Xaa Xaa Cys Xaa Xaa Cys Xaa
1 5 10 15

<210> SEQ ID NO 10
<211> LENGTH: 16
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (1)..(1)
<223> OTHER INFORMATION: Xaa can be any naturally occurring amino acid
<220> FEATURE:
<221> NAME/KEY: DISULFID
<222> LOCATION: (4)..(12)
<220> FEATURE:
<221> NAME/KEY: MISC_FEATURE
<222> LOCATION: (5)..(6)
<223> OTHER INFORMATION: Xaa can be any naturally occurring amino acid
<220> FEATURE:
<221> NAME/KEY: DISULFID
<222> LOCATION: (7)..(15)
<220> FEATURE:
<221> NAME/KEY: MISC_FEATURE
<222> LOCATION: (8)..(8)
<223> OTHER INFORMATION: Xaa can be any naturally occurring amino acid
<220> FEATURE:
<221> NAME/KEY: MISC_FEATURE
<222> LOCATION: (10)..(11)
<223> OTHER INFORMATION: Xaa can be any naturally occurring amino acid
<220> FEATURE:
<221> NAME/KEY: MISC_FEATURE
<222> LOCATION: (13)..(14)
<223> OTHER INFORMATION: Xaa can be any naturally occurring amino acid
<220> FEATURE:
<221> NAME/KEY: MISC_FEATURE
<222> LOCATION: (16)..(16)
<223> OTHER INFORMATION: Xaa can be any naturally occurring amino acid

<400> SEQUENCE: 10

Xaa Glu Glu Cys Xaa Xaa Cys Xaa Tyr Xaa Xaa Cys Xaa Xaa Cys Xaa
1 5 10 15

<210> SEQ ID NO 11
<211> LENGTH: 16
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (1)..(1)
<223> OTHER INFORMATION: Xaa can be any naturally occurring amino acid
<220> FEATURE:
<221> NAME/KEY: DISULFID
<222> LOCATION: (4)..(12)
<220> FEATURE:
<221> NAME/KEY: MISC_FEATURE
<222> LOCATION: (5)..(6)
<223> OTHER INFORMATION: Xaa can be any naturally occurring amino acid
<220> FEATURE:
<221> NAME/KEY: DISULFID
<222> LOCATION: (7)..(15)
<220> FEATURE:
<221> NAME/KEY: MISC_FEATURE
<222> LOCATION: (8)..(8)
<223> OTHER INFORMATION: Xaa can be any naturally occurring amino acid
<220> FEATURE:
<221> NAME/KEY: MISC_FEATURE
<222> LOCATION: (10)..(11)

-continued

<223> OTHER INFORMATION: Xaa can be any naturally occurring amino acid
<220> FEATURE:
<221> NAME/KEY: MISC_FEATURE
<222> LOCATION: (13)..(14)
<223> OTHER INFORMATION: Xaa can be any naturally occurring amino acid
<220> FEATURE:
<221> NAME/KEY: MISC_FEATURE
<222> LOCATION: (16)..(16)
<223> OTHER INFORMATION: Xaa can be any naturally occurring amino acid

<400> SEQUENCE: 11

Xaa Asp Glu Cys Xaa Xaa Cys Xaa Tyr Xaa Xaa Cys Xaa Xaa Cys Xaa
1 5 10 15

<210> SEQ ID NO 12
<211> LENGTH: 16
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (1)..(1)
<223> OTHER INFORMATION: Xaa can be any naturally occurring amino acid
<220> FEATURE:
<221> NAME/KEY: DISULFID
<222> LOCATION: (4)..(12)
<220> FEATURE:
<221> NAME/KEY: MISC_FEATURE
<222> LOCATION: (5)..(6)
<223> OTHER INFORMATION: Xaa can be any naturally occurring amino acid
<220> FEATURE:
<221> NAME/KEY: DISULFID
<222> LOCATION: (7)..(15)
<220> FEATURE:
<221> NAME/KEY: MISC_FEATURE
<222> LOCATION: (8)..(8)
<223> OTHER INFORMATION: Xaa can be any naturally occurring amino acid
<220> FEATURE:
<221> NAME/KEY: MISC_FEATURE
<222> LOCATION: (10)..(11)
<223> OTHER INFORMATION: Xaa can be any naturally occurring amino acid
<220> FEATURE:
<221> NAME/KEY: MISC_FEATURE
<222> LOCATION: (13)..(14)
<223> OTHER INFORMATION: Xaa can be any naturally occurring amino acid
<220> FEATURE:
<221> NAME/KEY: MISC_FEATURE
<222> LOCATION: (16)..(16)
<223> OTHER INFORMATION: Xaa can be any naturally occurring amino acid

<400> SEQUENCE: 12

Xaa Glu Asp Cys Xaa Xaa Cys Xaa Tyr Xaa Xaa Cys Xaa Xaa Cys Xaa
1 5 10 15

<210> SEQ ID NO 13
<211> LENGTH: 16
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (1)..(1)
<223> OTHER INFORMATION: Xaa can be any naturally occurring amino acid
<220> FEATURE:
<221> NAME/KEY: DISULFID
<222> LOCATION: (4)..(12)
<220> FEATURE:
<221> NAME/KEY: MISC_FEATURE
<222> LOCATION: (5)..(6)
<223> OTHER INFORMATION: Xaa can be any naturally occurring amino acid
<220> FEATURE:
<221> NAME/KEY: DISULFID
<222> LOCATION: (7)..(15)
<220> FEATURE:

<221> NAME/KEY: MISC_FEATURE
<222> LOCATION: (8)..(8)
<223> OTHER INFORMATION: Xaa can be any naturally occurring amino acid
<220> FEATURE:
<221> NAME/KEY: MISC_FEATURE
<222> LOCATION: (10)..(11)
<223> OTHER INFORMATION: Xaa can be any naturally occurring amino acid
<220> FEATURE:
<221> NAME/KEY: MISC_FEATURE
<222> LOCATION: (13)..(14)
<223> OTHER INFORMATION: Xaa can be any naturally occurring amino acid
<220> FEATURE:
<221> NAME/KEY: MISC_FEATURE
<222> LOCATION: (16)..(16)
<223> OTHER INFORMATION: Xaa can be any naturally occurring amino acid

<400> SEQUENCE: 13

Xaa Asp Asp Cys Xaa Xaa Cys Xaa Gln Xaa Xaa Cys Xaa Xaa Cys Xaa
1               5                   10                  15

<210> SEQ ID NO 14
<211> LENGTH: 16
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (1)..(1)
<223> OTHER INFORMATION: Xaa can be any naturally occurring amino acid
<220> FEATURE:
<221> NAME/KEY: DISULFID
<222> LOCATION: (4)..(12)
<220> FEATURE:
<221> NAME/KEY: MISC_FEATURE
<222> LOCATION: (5)..(6)
<223> OTHER INFORMATION: Xaa can be any naturally occurring amino acid
<220> FEATURE:
<221> NAME/KEY: DISULFID
<222> LOCATION: (7)..(15)
<220> FEATURE:
<221> NAME/KEY: MISC_FEATURE
<222> LOCATION: (8)..(8)
<223> OTHER INFORMATION: Xaa can be any naturally occurring amino acid
<220> FEATURE:
<221> NAME/KEY: MISC_FEATURE
<222> LOCATION: (10)..(11)
<223> OTHER INFORMATION: Xaa can be any naturally occurring amino acid
<220> FEATURE:
<221> NAME/KEY: MISC_FEATURE
<222> LOCATION: (13)..(14)
<223> OTHER INFORMATION: Xaa can be any naturally occurring amino acid
<220> FEATURE:
<221> NAME/KEY: MISC_FEATURE
<222> LOCATION: (16)..(16)
<223> OTHER INFORMATION: Xaa can be any naturally occurring amino acid

<400> SEQUENCE: 14

Xaa Glu Glu Cys Xaa Xaa Cys Xaa Gln Xaa Xaa Cys Xaa Xaa Cys Xaa
1               5                   10                  15

<210> SEQ ID NO 15
<211> LENGTH: 16
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (1)..(1)
<223> OTHER INFORMATION: Xaa can be any naturally occurring amino acid
<220> FEATURE:
<221> NAME/KEY: DISULFID
<222> LOCATION: (4)..(12)
<220> FEATURE:
<221> NAME/KEY: MISC_FEATURE

```
<222> LOCATION: (5)..(6)
<223> OTHER INFORMATION: Xaa can be any naturally occurring amino acid
<220> FEATURE:
<221> NAME/KEY: DISULFID
<222> LOCATION: (7)..(15)
<220> FEATURE:
<221> NAME/KEY: MISC_FEATURE
<222> LOCATION: (8)..(8)
<223> OTHER INFORMATION: Xaa can be any naturally occurring amino acid
<220> FEATURE:
<221> NAME/KEY: MISC_FEATURE
<222> LOCATION: (10)..(11)
<223> OTHER INFORMATION: Xaa can be any naturally occurring amino acid
<220> FEATURE:
<221> NAME/KEY: MISC_FEATURE
<222> LOCATION: (13)..(14)
<223> OTHER INFORMATION: Xaa can be any naturally occurring amino acid
<220> FEATURE:
<221> NAME/KEY: MISC_FEATURE
<222> LOCATION: (16)..(16)
<223> OTHER INFORMATION: Xaa can be any naturally occurring amino acid

<400> SEQUENCE: 15

Xaa Asp Glu Cys Xaa Xaa Cys Xaa Gln Xaa Xaa Cys Xaa Xaa Cys Xaa
1               5                   10                  15


<210> SEQ ID NO 16
<211> LENGTH: 16
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (1)..(1)
<223> OTHER INFORMATION: Xaa can be any naturally occurring amino acid
<220> FEATURE:
<221> NAME/KEY: DISULFID
<222> LOCATION: (4)..(12)
<220> FEATURE:
<221> NAME/KEY: MISC_FEATURE
<222> LOCATION: (5)..(6)
<223> OTHER INFORMATION: Xaa can be any naturally occurring amino acid
<220> FEATURE:
<221> NAME/KEY: DISULFID
<222> LOCATION: (7)..(15)
<220> FEATURE:
<221> NAME/KEY: MISC_FEATURE
<222> LOCATION: (8)..(8)
<223> OTHER INFORMATION: Xaa can be any naturally occurring amino acid
<220> FEATURE:
<221> NAME/KEY: MISC_FEATURE
<222> LOCATION: (10)..(11)
<223> OTHER INFORMATION: Xaa can be any naturally occurring amino acid
<220> FEATURE:
<221> NAME/KEY: MISC_FEATURE
<222> LOCATION: (13)..(14)
<223> OTHER INFORMATION: Xaa can be any naturally occurring amino acid
<220> FEATURE:
<221> NAME/KEY: MISC_FEATURE
<222> LOCATION: (16)..(16)
<223> OTHER INFORMATION: Xaa can be any naturally occurring amino acid

<400> SEQUENCE: 16

Xaa Glu Asp Cys Xaa Xaa Cys Xaa Gln Xaa Xaa Cys Xaa Xaa Cys Xaa
1               5                   10                  15


<210> SEQ ID NO 17
<211> LENGTH: 14
<212> TYPE: PRT
<213> ORGANISM: Artificial Sequence
<220> FEATURE:
<223> OTHER INFORMATION: Chemically synthesized peptide
<220> FEATURE:
<221> NAME/KEY: DISULFID
<222> LOCATION: (2)..(10)
```

-continued

<220> FEATURE:
<221> NAME/KEY: MISC_FEATURE
<222> LOCATION: (3)..(4)
<223> OTHER INFORMATION: Xaa can be any naturally occurring amino acid
<220> FEATURE:
<221> NAME/KEY: DISULFID
<222> LOCATION: (5)..(13)
<220> FEATURE:
<221> NAME/KEY: MISC_FEATURE
<222> LOCATION: (6)..(6)
<223> OTHER INFORMATION: Xaa can be any naturally occurring amino acid
<220> FEATURE:
<221> NAME/KEY: MISC_FEATURE
<222> LOCATION: (8)..(9)
<223> OTHER INFORMATION: Xaa can be any naturally occurring amino acid
<220> FEATURE:
<221> NAME/KEY: MISC_FEATURE
<222> LOCATION: (11)..(12)
<223> OTHER INFORMATION: Xaa can be any naturally occurring amino acid
<220> FEATURE:
<221> NAME/KEY: MISC_FEATURE
<222> LOCATION: (14)..(14)
<223> OTHER INFORMATION: Xaa can be any naturally occurring amino acid

<400> SEQUENCE: 17

Glu Cys Xaa Xaa Cys Xaa Asn Xaa Xaa Cys Xaa Xaa Cys Xaa
1               5                   10

<210> SEQ ID NO 18
<211> LENGTH: 13
<212> TYPE: PRT
<213> ORGANISM: Artificial Sequence
<220> FEATURE:
<223> OTHER INFORMATION: Chemically synthesized peptide
<220> FEATURE:
<221> NAME/KEY: DISULFID
<222> LOCATION: (2)..(10)
<220> FEATURE:
<221> NAME/KEY: MISC_FEATURE
<222> LOCATION: (3)..(4)
<223> OTHER INFORMATION: Xaa can be any naturally occurring amino acid
<220> FEATURE:
<221> NAME/KEY: DISULFID
<222> LOCATION: (5)..(13)
<220> FEATURE:
<221> NAME/KEY: MISC_FEATURE
<222> LOCATION: (6)..(6)
<223> OTHER INFORMATION: Xaa can be any naturally occurring amino acid
<220> FEATURE:
<221> NAME/KEY: MISC_FEATURE
<222> LOCATION: (8)..(9)
<223> OTHER INFORMATION: Xaa can be any naturally occurring amino acid
<220> FEATURE:
<221> NAME/KEY: MISC_FEATURE
<222> LOCATION: (11)..(12)
<223> OTHER INFORMATION: Xaa can be any naturally occurring amino acid

<400> SEQUENCE: 18

Glu Cys Xaa Xaa Cys Xaa Asn Xaa Xaa Cys Xaa Xaa Cys
1               5                   10

<210> SEQ ID NO 19
<211> LENGTH: 15
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (1)..(1)
<223> OTHER INFORMATION: Xaa can be any naturally occurring amino acid
<220> FEATURE:
<221> NAME/KEY: DISULFID
<222> LOCATION: (3)..(11)
<220> FEATURE:
<221> NAME/KEY: MISC_FEATURE -continued

```
<222> LOCATION: (4)..(5)
<223> OTHER INFORMATION: Xaa can be any naturally occurring amino acid
<220> FEATURE:
<221> NAME/KEY: DISULFID
<222> LOCATION: (6)..(14)
<220> FEATURE:
<221> NAME/KEY: MISC_FEATURE
<222> LOCATION: (7)..(7)
<223> OTHER INFORMATION: Xaa can be any naturally occurring amino acid
<220> FEATURE:
<221> NAME/KEY: MISC_FEATURE
<222> LOCATION: (9)..(10)
<223> OTHER INFORMATION: Xaa can be any naturally occurring amino acid
<220> FEATURE:
<221> NAME/KEY: MISC_FEATURE
<222> LOCATION: (12)..(13)
<223> OTHER INFORMATION: Xaa can be any naturally occurring amino acid
<220> FEATURE:
<221> NAME/KEY: MISC_FEATURE
<222> LOCATION: (15)..(15)
<223> OTHER INFORMATION: Xaa can be any naturally occurring amino acid

<400> SEQUENCE: 19

Xaa Glu Cys Xaa Xaa Cys Xaa Asn Xaa Xaa Cys Xaa Xaa Cys Xaa
1               5                   10                  15


<210> SEQ ID NO 20
<211> LENGTH: 16
<212> TYPE: PRT
<213> ORGANISM: Artificial Sequence
<220> FEATURE:
<223> OTHER INFORMATION: Chemically synthesized peptide
<220> FEATURE:
<221> NAME/KEY: DISULFID
<222> LOCATION: (4)..(12)
<220> FEATURE:
<221> NAME/KEY: DISULFID
<222> LOCATION: (7)..(15)

<400> SEQUENCE: 20

Asn Asp Glu Cys Glu Leu Cys Val Asn Val Ala Cys Thr Gly Cys Leu
1               5                   10                  15


<210> SEQ ID NO 21
<211> LENGTH: 14
<212> TYPE: PRT
<213> ORGANISM: Artificial Sequence
<220> FEATURE:
<223> OTHER INFORMATION: Chemically synthesized peptide
<220> FEATURE:
<221> NAME/KEY: DISULFID
<222> LOCATION: (2)..(10)
<220> FEATURE:
<221> NAME/KEY: DISULFID
<222> LOCATION: (5)..(13)

<400> SEQUENCE: 21

Glu Cys Glu Leu Cys Val Asn Val Ala Cys Thr Gly Cys Leu
1               5                   10


<210> SEQ ID NO 22
<211> LENGTH: 15
<212> TYPE: PRT
<213> ORGANISM: Homo sapiens
<220> FEATURE:
<221> NAME/KEY: DISULFID
<222> LOCATION: (4)..(12)
<220> FEATURE:
<221> NAME/KEY: DISULFID
<222> LOCATION: (7)..(15)

<400> SEQUENCE: 22

Pro Gly Thr Cys Glu Ile Cys Ala Tyr Ala Ala Cys Thr Gly Cys
```

-continued

```
1               5                   10                  15


<210> SEQ ID NO 23
<211> LENGTH: 19
<212> TYPE: PRT
<213> ORGANISM: Escherichia coli
<220> FEATURE:
<221> NAME/KEY: DISULFID
<222> LOCATION: (6)..(10)
<220> FEATURE:
<221> NAME/KEY: DISULFID
<222> LOCATION: (7)..(15)
<220> FEATURE:
<221> NAME/KEY: DISULFID
<222> LOCATION: (11)..(18)

<400> SEQUENCE: 23

Asn Ser Ser Asn Tyr Cys Cys Glu Leu Cys Cys Asn Pro Ala Cys Thr
1               5                   10                  15

Gly Cys Tyr
```

GUANYLATE CYCLASE RECEPTOR AGONISTS FOR THE TREATMENT OF TISSUE INFLAMMATION AND CARCINOGENESIS

RELATED APPLICATIONS

The present application is a continuation of U.S. patent application Ser. No. 11/347,115 filed Feb. 2, 2006, now U.S. Pat. No. 7,799,897, which is a continuation of U.S. patent application Ser. No. 10/107,814, filed Mar. 28, 2002, now U.S. Pat. No. 7,041,786 and claims the benefit of U.S. Patent Application No. 60/279,438, filed on Mar. 29, 2001; U.S. Patent Application No. 60/279,437, filed on Mar. 29, 2001; U.S. Patent Application No. 60/300,850, filed on Jun. 27, 2001; U.S. Patent Application No. 60/303,806, filed on Jul. 10, 2001; U.S. Patent Application No. 60/307,358, filed on Jul. 25, 2001; and U.S. Patent Application No. 60/348,646, filed on Jan. 17, 2002. The contents of these applications are incorporated by reference in their entireties.

INCORPORATION-BY-REFERENCE OF SEQUENCE LISTING

The contents of the text file named "40737-501C02US_ST25.txt", which was created on Mar. 29, 2011 and is 18.8 KB in size, are hereby incorporated by reference in their entirety.

FIELD OF THE INVENTION

The present invention relates to the therapeutic use of guanylate cyclase receptor agonists as a means for enhancing the intracellular production of cGMP. The agonists may be used either alone or in combination with inhibitors of cGMP-specific phosphodiesterase to prevent or treat cancerous, pre-cancerous and metastatic growths, particularly in the gastrointestinal tract and lungs. In addition, the agonists may be used in the treatment of inflammatory disorders such as ulcerative colitis and asthma.

BACKGROUND OF THE INVENTION

Uroguanylin, guanylin and bacterial ST peptides are structurally related peptides that bind to a guanylate cyclase receptor and stimulate intracellular production of cyclic guanosine monophosphate (cGMP) (1-6). This results in the activation of the cystic fibrosis transmembrane conductance regulator (CFTR), an apical membrane channel for efflux of chloride from enterocytes lining the intestinal tract (1-6). Activation of CFTR and the subsequent enhancement of transepithelial secretion of chloride leads to stimulation of sodium and water secretion into the intestinal lumen. Therefore, by serving as paracrine regulators of CFTR activity, cGMP receptor agonists regulate fluid and electrolyte transport in the GI tract (1-6; U.S. Pat. No. 5,489,670).

The process of epithelial renewal involves the proliferation, migration, differentiation, senescence, and eventual loss of GI cells in the lumen (7,8). The GI mucosa can be divided into three distinct zones based on the proliferation index of epithelial cells. One of these zones, the proliferative zone, consists of undifferentiated stem cells responsible for providing a constant source of new cells. The stem cells migrate upward toward the lumen to which they are extruded. As they migrate, the cells lose their capacity to divide and become differentiated for carrying out specialized functions of the GI mucosa (9). Renewal of GI mucosa is very rapid with complete turnover occurring within a 24-48 hour period (9). During this process mutated and unwanted cells are replenished with new cells. Hence, homeostasis of the GI mucosa is regulated by continual maintenance of the balance between proliferation and apoptotic rates (8).

The rates of cell proliferation and apoptosis in the gut epithelium can be increased or decreased in a wide variety of different circumstances, e.g., in response to physiological stimuli such as aging, inflammatory signals, hormones, peptides, growth factors, chemicals and dietary habits. In addition, an enhanced proliferation rate is frequently associated with a reduction in turnover time and an expansion of the proliferative zone (10). The proliferation index has been observed to be much higher in pathological cases of ulcerative colitis and other GI disorders (11). Thus, intestinal hyperplasia is the major promoter of gastrointestinal inflammation and carcinogenesis.

In addition to a role for uroguanylin and guanylin as modulators of intestinal fluid and ion secretion, these peptides may also be involved in the continual renewal of GI mucosa. Previously published data in WO 01/25266 suggests a peptide with the active domain of uroguanylin may function as an inhibitor of polyp development in the colon and may constitute a treatment of colon cancer. However, the mechanism by which this is claimed to occur is questionable in that WO 01/25266 teaches uroguanylin agonist peptides that bind specifically to a guanylate cyclase receptor, termed GC-C, that was first described as the receptor for *E. coli* heat-stable enterotoxin (ST) (4). Knockout mice lacking this guanylate cyclase receptor show resistance to ST in intestine, but effects of uroguanylin and ST are not disturbed in the kidney in vivo (3). These results were further supported by the fact that membrane depolarization induced by guanylin was blocked by genistein, a tyrosine kinase inhibitor, whereas hyperpolarization induced by uroguanylin was not effected (12,13). Taken together these data suggest that uroguanylin also binds to a currently unknown receptor, which is distinct from GC-C.

Other papers have reported that production of uroguanylin and guanylin is dramatically decreased in pre-cancerous colon polyps and tumor tissues (14-17). In addition, genes for both uroguanylin and guanylin have been shown to be localized to regions of the genome frequently associated with loss of heterozygosity in human colon carcinoma (18-20). Taken together, these findings indicate that uroguanylin, guanylin and other peptides with similar activity may be used in the prevention or treatment of abnormal colon growths. This proposal is bolstered by a recent study demonstrating oral administration of uroguanylin inhibits polyp formation in mice (15,16).

Uroguanylin and guanylin peptides also appear to promote apoptosis by controlling cellular ion flux. Alterations in apoptosis have been associated with tumor progression to the metastatic phenotype. While a primary gastrointestinal (GI) cancer is limited to the small intestine, colon, and rectum, it may metastasize and spread to such localities as bone, lymph nodes, liver, lung, peritoneum, ovaries, brain. By enhancing the efflux of $K^+$ and influx of $Ca^{++}$, uroguanylin and related peptides may promote the death of transformed cells and thereby inhibit metastasis.

One of the clinical manifestations of reduced CFTR activity is the inflammation of airway passages (21). This effect may be due to CTFR regulating the expression of NF-KB, chemokines and cytokines (22-25). Recent reports have also suggested that the CFTR channel is involved in the transport and maintenance of reduced glutathione, an antioxidant that plays an important role in protecting against inflammation caused by oxidative stress (39). Enhancement of intracellular levels of cGMP by way of guanylate cyclase activation or by way of inhibition of cGMP-specific phosphodiesterase would be expected to down-regulate these inflammatory stimuli. Thus, uroguanylin-type agonists should be useful in the prevention and treatment of inflammatory diseases of the lung (e.g., asthma), bowel (e.g., ulcerative colitis and Crohn's disease), pancreas and other organs.

Overall, it may be concluded that agonists of guanylate cyclase receptor such as uroguanylin have potential therapeutic value in the treatment of a wide variety of inflammatory conditions, cancer (particularly colon cancer) and as anti-metastatic agents. The development of new agonists is therefore of substantial clinical importance.

SUMMARY OF THE INVENTION

The present invention is based upon the development of new agonists of guanylate cyclase receptor, and new uses of naturally occurring agonists. The agonists are analogs of uroguanylin, many of which have superior properties either in terms of improved receptor activation, stability, activity at low pH or reduced adverse effects. The peptides may be used to treat any condition that responds to enhanced intracellular levels of cGMP. Intracellular levels of cGMP can be increased by enhancing intracellular production of cGMP and/or by inhibition of its degradation by cGMP-specific phosphodiesterases. Among the specific conditions that can be treated or prevented are inflammatory conditions, cancer, polyps, and metastasis.

In its first aspect, the present invention is directed to a peptide consisting essentially of the amino acid sequence of any one of SEQ ID NOs:2-21 and to therapeutic compositions which contain these peptides. The term "consisting essentially of" includes peptides that are identical to a recited sequence identification number and other sequences that do not differ substantially in terms of either structure or function. For the purpose of the present application, a peptide differs substantially if its structure varies by more than three amino acids from a peptide of SEQ ID NOs:2-21 or if its activation of cellular cGMP production is reduced or enhanced by more than 50%. Preferably, substantially similar peptides should differ by no more than two amino acids and not differ by more than about 25% with respect to activating cGMP production. The most preferred peptide is a bicycle having the sequence of SEQ ID NO:20.

The peptides may be in a pharmaceutical composition in unit dose form, together with one or more pharmaceutically acceptable excipients. The term "unit dose form" refers to a single drug delivery entity, e.g., a tablet, capsule, solution or inhalation formulation. The amount of peptide present should be sufficient to have a positive therapeutic effect when administered to a patient (typically, between 100 μg and 3 g). What constitutes a "positive therapeutic effect" will depend upon the particular condition being treated and will include any significant improvement in a condition readily recognized by one of skill in the art. For example, it may constitute a reduction in inflammation, a shrinkage of polyps or tumors, a reduction in metastatic lesions, etc.

The invention also encompasses combination therapy utilizing a guanylate cyclase receptor agonist administered either alone or together with an inhibitor of cGMP-dependent phosphodiesterase, an anti-inflammatory agent or an anticancer agent. These agents should be present in amounts known in the art to be therapeutically effective when administered to a patient. Anti-neoplastic agents may include alkylating agents, epipodophyllotoxins, nitrosoureas, antimetabolites, vinca alkaloids, anthracycline antibiotics, nitrogen mustard agents, and the like. Particular anti-neoplastic agents may include tamoxifen, TAXOL™, etoposide and 5-fluorouracil. Antiviral and monoclonal antibody therapies may be combined with chemotherapeutic compositions comprising at least one guanylate cyclase receptor agonist in devising a treatment regimen tailored to a patient's specific needs.

In another aspect, the invention is directed to a method for preventing, treating or retarding the onset of cancer, particularly cancer of epithelial cells, or polyps in a subject by administering a composition comprising an effective amount of a guanylate cyclase receptor agonist, preferably a synthetic guanylate cyclase receptor agonist. The term "effective amount" refers to sufficient agonist to measurably increase intracellular levels of cGMP. The term "synthetic" refers to a peptide created to bind a guanylate cyclase receptor, but containing certain amino acid sequence substitutions not present in known endogenous guanylate cyclase agonists, such as uroguanylin. The agonist should be a peptide selected from those defined by SEQ ID NOs:2-21 and which are listed in Tables 2 and 3. Also included in the invention are methods of treating primary cancers, other than primary colon cancer, by administering an effective dosage of a peptide selected from the group consisting of: uroguanylin; guanylin; and *E. coli* ST peptide. Any known form of uroguanylin or guanylin can be used for this purpose, although the human peptides are preferred.

The invention also includes methods of preventing or treating tumor metastasis from a primary tumor mass. Metastatic tumor cells having guanylate cyclase receptors may be targeted by peptides generated according to the invention. In a preferred embodiment, the targeted receptor is found on cells of gastrointestinal (GI) cancers and on metastasized cells derived from those cancers. Such receptors are typically transmembrane proteins with an extracellular ligand-binding domain, a membrane-spanning domain, and an intracellular domain with guanylate cyclase activity. Although the invention is not bound by any particular mechanism of action, it is believed that the peptides will act by binding to these cellular receptors and inducing apoptosis. Metastatic tumors may also be treated by administering any known form of uroguanylin or guanylin (preferably human) or by administering *E. coli* ST peptide.

Peptides may be administered either alone or together with one or more inhibitors of cGMP dependent phosphodiesterase. Examples of cGMP dependent phosphodiesterase inhibitors include suldinac sulfone, zaprinast, and motapizone. Treatable forms of cancer include breast cancer, colorectal cancer, lung cancer, ovarian cancer, pancreatic cancer, prostate cancer, renal cancer, and testicular cancer. Colon carcinogenesis may be prevented by inhibiting pre-cancerous colorectal polyp development via administration of a composition according to the invention. It is believed that the peptides should be especially effective with respect to the treatment of colon cancer and in preventing the metastasis of colon tumors.

In another aspect, the invention is directed to a method for treating, preventing, or retarding the onset of organ inflammation (e.g., inflammation associated with the GI tract, asthma, nephritis, hepatitis, pancreatitis, bronchitis, or cystic fibrosis) of a subject by administering a composition comprising an agonist of a guanylate cyclase receptor that enhances intracellular production of cGMP. Preferred peptide agonists are selected from the group defined by SEQ ID NOs:2-21 shown in Tables 2 and 3, or uroguanylin, or guanylin, or *E. coli* ST peptide. These peptides may optionally be administered with one or more inhibitors of cGMP dependent phosphodiesterase, e.g., suldinac sulfone, zaprinast, or motapizone. In a preferred embodiment, the invention is directed to a method of treating an inflammatory disorder in a mammalian gastrointestinal tract. The inflammatory disorder may be classified as an inflammatory bowel disease, and more particularly may be Crohn's disease or ulcerative colitis. Administration may be enteric, and employ formulations tailored to target enterocytes.

In a broader sense, the invention includes methods of inducing apoptosis in a patient by administering an effective amount of a peptide having the sequence of any one of SEQ ID NO:2-SEQ ID NO:21, or uroguanylin, or guanylin or *E. coli* ST peptide. An "effective amount" of peptide, in this sense, refers to an amount sufficient to increase apoptosis in a target tissue. For example, sufficient peptide may be given to induce an increased rate of cell death in a neoplastic growth.

The most preferred peptide for use in the methods described above is the peptide defined by SEQ ID NO:20. The sequence is as follows (see also Table 3):

```
Asn¹ Asp² Glu³ Cys⁴ Glu⁵ Leu⁶ Cys⁷ Val⁸ Asn⁹ Val¹⁰ Ala¹¹ Cys¹² Thr¹³ Gly¹⁴ Cys¹⁵ Leu¹⁶
               *              **                      *                  **
```

and wherein there is one disulfide linkage between the cysteine at position 4 and the cysteine at position 12; and a second disulfide linkage between the cysteine at position 7 and the cysteine at position 15 (SEQ ID NO:20). This peptide has been found to have enhanced biological activity as an agonist of cGMP production due to its enhanced binding constant for the guanylate cyclase receptor, and is superior to uroguanylin with regard to temperature and protease stability and with regard to its biological activity at the physiologically favorable pH range (pH 6 to 7) in the large intestine.

The guanylate cyclase receptor agonists used in the methods described above may be administered either orally, systemically or locally. Dosage forms include preparations for inhalation or injection, solutions, suspensions, emulsions, tablets, capsules, topical salves and lotions, transdermal compositions, other known peptide formulations and pegylated peptide analogs. An effective dosage of the composition will typically be between about 1 .mu.g and about 10 mg per kilogram body weight, preferably between about 10 μg to 5 mg of the compound per kilogram body weight. Adjustments in dosage will be made using methods that are routine in the art and will be based upon the particular composition being used and clinical considerations. Agonists may be administered as either the sole active agent or in combination with other drugs, e.g., an inhibitor of cGMP-dependent phosphodiesterase. In all cases, additional drugs should be administered at a dosage that is therapeutically effective using the existing art as a guide. Drugs may be administered in a single composition or sequentially.

DETAILED DESCRIPTION OF THE INVENTION

The present invention is based upon several concepts. The first is that there is a cGMP-dependent mechanism which regulates the balance between cellular proliferation and apoptosis and that a reduction in cGMP levels, due to a deficiency of uroguanylin/guanylin and/or due to the activation of cGMP-specific phosphodiesterases, is an early and critical step in neoplastic transformation. A second concept is that the release of arachidonic acid from membrane phospholipids, which leads to the activation of $cPLA_2$, COX-2 and possibly 5-lipoxygenase during the process of inflammation, is down-regulated by a cGMP-dependent mechanism, leading to reduced levels of prostaglandins and leukotrienes, and that increasing intracellular levels of cGMP may therefore produce an anti-inflammatory response. In addition, a cGMP-dependent mechanism, is thought to be involved in the control of proinflammatory processes. Therefore, elevating intracellular levels of cGMP may be used as a means of treating and controlling inflammatory bowel diseases such as ulcerative colitis and Crohn's disease and other organ inflammation (e.g., associated with asthma, nephritis, hepatitis, pancreatitis, bronchitis, cystic fibrosis).

Without intending to be bound by any theory, it is envisioned that ion transport across the plasma membrane may prove to be an important regulator of the balance between cell proliferation and apoptosis that will be affected by compositions altering cGMP concentrations. Uroguanylin has been shown to stimulate $K^+$ efflux, $Ca^{++}$ influx and water transport in the gastrointestinal tract (3). Moreover, atrial natriuretic peptide (ANP), a peptide that also binds to a specific guanylate cyclase receptor, has also been shown to induce apoptosis in rat mesangial cells, and to induce apoptosis in cardiac myocytes by a cGMP mechanism (26-29). It is believed that binding of the present agonists to a guanylate cyclase receptor stimulates production of cGMP. This ligand-receptor interaction, via activation of a cascade of cGMP-dependent protein kinases and CFTR, is then expected to induce apoptosis in target cells. Therefore, administration of the novel peptides defined by SEQ ID NOs:2-21, as shown in Tables 2 and 3, or uroguanylin, or guanylin or *E. coli* ST peptide is expected to eliminate or, at least retard, the onset of inflammatory diseases of the GI tract and general organ inflammation (e.g., asthma, nephritis, hepatitis, pancreatitis, bronchitis, cystic fibrosis).

In another aspect, the invention is directed to a method for preventing, treating or retarding the onset of cancer, particularly cancer of epithelial cells, in a subject by administering a composition comprising an effective amount of a guanylate cyclase receptor agonist, preferably a synthetic a guanylate cyclase receptor agonist. The term "effective amount" refers to sufficient agonist to measurably increase intracellular levels of cGMP. The term "synthetic" refers to a peptide created to bind a guanylate cyclase receptor, but containing certain amino acid sequence substitutions not present in known endogenous guanylate cyclase agonists, such as uroguanylin. The agonist should be a peptide selected from those defined by SEQ ID NOs:2-21 and which are listed in Tables 2 and 3. Also included in the invention are methods of treating primary and metastatic cancers, other than primary colon cancer, by administering an effective dosage of a peptide selected from the group consisting of: uroguanylin; guanylin; and *E. coli* ST peptide. Any known form of uroguanylin or guanylin can be used for this purpose, although the human peptides are preferred.

The cGMP-dependent mechanism that regulates the balance between cellular proliferation and apoptosis in metastatic tumor cells may serve as a mechanism for targeting and treating metastatic tumors. The liver is the most common site of metastasis from a primary colorectal cancer. Toward later stages of disease, colorectal metastatic cells may also invade other parts of the body. It is important to note that metastatic cells originating from the primary site in the gastrointestinal tract typically continue to express guanylate cyclase receptors and therefore, these cells should be sensitive to apoptosis therapy mediated by intestinal guanylate cyclase receptors.

Peptides having uroguanylin activity, when used either alone or in combination with specific inhibitors of cGMP-phosphodiesterase, also retard the onset of carcinogenesis in gut epithelium by restoring a healthy balance between cell proliferation and apoptosis via a cGMP-mediated mechanism.

As used herein, the term "guanylate cyclase receptor" refers to the class of guanylate cyclase receptors on any cell type to which the inventive agonist peptides or natural agonists described herein bind.

As used herein, the term "guanylate cyclase receptor-agonist" refers to peptides and/or other compounds that bind to a guanylate cyclase receptor and stimulate cGMP production. The term also includes all peptides that have amino acid sequences substantially equivalent to at least a portion of the binding domain comprising amino acid residues 3-15 of SEQ ID NO: 1. This term also covers fragments and pro-peptides that bind to guanylate cyclase receptor and stimulate cGMP production. The term "substantially equivalent" refers to a peptide that has an amino acid sequence equivalent to that of the binding domain where certain residues may be deleted or replaced with other amino acids without impairing the peptide's ability to bind to a guanylate cyclase receptor and stimulate cGMP production.

Strategy and Design of Novel Guanylate Cyclase Receptor Agonists

Uroguanylin is a peptide secreted by the goblet and other epithelial cells lining the gastrointestinal mucosa as pro-uroguanylin, a functionally inactive form. The human pro-peptide is subsequently converted to the functionally active 16 amino acid peptide set forth in SEQ ID NO:1 (human uroguanylin sequence, see Table 2) in the lumen of the intestine by endogenous proteases. Since uroguanylin is a heat-resistant, acid-resistant, and proteolysis-resistant peptide, oral or systemic administration of this peptide and/or other peptides similar to the functionally active 16 amino acid peptide sequence of SEQ ID NO:1 may be effectively employed in treatment methods.

Peptides similar to, but distinct from, uroguanylin are described below, including some which produce superior cGMP enhancing properties and/or other beneficial characteristics (e.g., improved temperature stability, enhanced protease stability, or superior activity at preferred pH's) compared to previously known uroguanylin peptides. The peptides may be used to inhibit GI inflammation and for treating or preventing the onset of polyp formation associated with gut inflammation. Epithelial tissues susceptible to cancer cell formation may also be treated. The guanylate cyclase receptor agonists described have the amino acid sequences shown in Tables 2 and 3. The "binding domain" for agonist-receptor interaction includes the amino acid residues from 3-15 of SEQ ID NO:1.

Molecular modeling was applied to the design of novel guanylate cyclase receptor agonists using methods detailed in (30). It consisted of energy calculations for three compounds known to interact with guanylate cyclase receptors, namely for human uroguanylin, bicyclo[4,12; 7,15]Asn$^1$-Asp$^2$-Asp$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Leu$^{16}$ (UG, SEQ ID NO:1); human guanylin, bicyclo [4,12; 7,15]Pro$^1$-Gly$^2$-Thr$^3$-Cys$^4$-Glu$^5$-Ile$^6$-Cys$^7$-Ala$^8$-Tyr$^9$-Ala$^{10}$-Ala$^{11}$-Cys$^{12}$-Thr$^{13}$-Gly$^{14}$-$^{15}$Cys (GU, SEQ ID NO:22); and *E. coli* small heat-stable enterotoxin, tricyclo [6,10; 7,15; 11-18] Asn$^1$-Ser$^2$-Ser$^3$-Asn$^4$-Tyr$^5$-Cys$^6$-Cys$^7$-Glu$^8$-Leu$^9$-Cys$^{10}$-Cys$^{11}$-Asn$^{12}$-Pro$^{13}$-Ala$^{14}$-Cys$^{15}$-Thr$^{16}$-Gly$^{17}$-Cys$^{18}$-Tyr$^{19}$ (ST, SEQ ID NO:23). Geometrical comparisons of all possible low-energy conformations for these three compounds were used to reveal the common 3D structures that served as the "templates" for the bioactive conformation, i.e., for the conformation presumably adopted by GU, UG and ST during interaction with receptor. It allowed designing novel analogs with significantly increased conformational population of the bioactive conformation at the expense of other low-energy conformations by selecting individual substitutions for various amino acid residues.

Energy calculations were performed by use of build-up procedures (30). The ECEPP/2 potential field (31,32) was used assuming rigid valence geometry with planar trans-peptide bonds, including that for Pro$^{13}$ in ST. The ω angle in Pro$^{13}$ was allowed to vary. Aliphatic and aromatic hydrogens were generally included in united atomic centers of $CH_n$ type; $H^{\alpha}$-atoms and amide hydrogens were described explicitly.

The main calculation scheme involved several successive steps. First, the sequences of the two monocyclic model fragments (three fragments for ST), Ac-cyclo (Cys$^i$-. . . -Cys$^j$)—NMe, were considered, where all residues except Cys, Gly and Pro were replaced by alanines; the i and j values corresponded to the sequences of GU, UG and ST. At this step, all possible combinations of local minima for the peptide backbone for each amino acid residue were considered, i.e., the minima in the Ramachandran map of E, F, C, D, A and A* types (according to the notation in (33)) for the Ala residue; of E*, F*, C*, D*, A, E, F, C D and A* types for the Gly residue; and of F, C and A types for Pro. For each backbone conformation, one optimal possibility to close a cycle employing the parabolic potential functions, intrinsic to the ECEPP force field, was found by checking an energy profile of rotation around the dihedral angle χ1 for the D-Cys residue.

Totally, as many as ca. 180,000 conformations for each of the cyclic moieties were considered. Then, the conformers satisfying the $E-E_{min}<\Delta E=15$ kcal/mol criterion and differing by more than 40° in at least one value of any backbone dihedral angle were selected (from ca. 3,000 to 8,000 conformations for different model fragments). At the next step, the selected conformations of the matching monocyclic fragments were overlapped to create possible conformations of the bicyclic model fragments (the tricyclic fragments in the case of ST). Typically, this procedure yielded ca. 20,000-30,000 conformations. All these conformations were submitted for a new cycle of energy calculations, which resulted in 191 conformations satisfying the $E-E_{min}<\Delta E=20$ kcal/mol criterion for the ST model fragment and in 6,965 conformations satisfying the same criterion for the GU/UG model fragment. After that, the missing side chains in the model fragments were restored, and energy calculations were performed again, the dihedral angle values of side chain groups (except the χ1 angle for the Cys residues) and of the terminal groups of the backbone being optimized before energy minimization to achieve their most favorable spatial arrangements, employing an algorithm previously described (34). For the UG 4-15 fragment, 632 conformations satisfied the criterion of ΔE=20 kcal/mol; 164 of them satisfied the more stringent criterion of ΔE=12 kcal/mol, which corresponds to the accepted criterion of 1 kcal/mol/residue (30). Subsequent elongation of the UG 4-15 fragment to 3-16, and then to the entire UG molecule was performed by the same build-up procedure. Finally, 31 backbone conformations of UG were found as satisfying the criterion of ΔE=16 kcal/mol.

Geometrical comparison of conformers was performed in the following manner. The best fit in the superposition for the atomic centers in a pair of conformers was assessed to check the level of geometrical similarity between the two conformers, according to (35). The criterion for geometrical similarity was the rms value, which was calculated for a pair of conformations A and B as follows:

$$rms=(1/N)\Sigma^N i=1[(x^A i-x^B i)^2+(y^A i-y^B i)^2+(z^A i-z^B i)^2]^{1/2},$$

where N is the number of the $C^\alpha$-atom pairs chosen for superposition, and x, y and z are the Cartesian coordinates. By the criterion of geometrical similarity of rms<2.0 Å, low-energy conformations of the rigid conformational fragment UG 4-15 fell into seven conformational families. One of them consists of the same six conformers that are similar both to 1UYA and 1ETN; this family contains also the lowest-energy conformer of UG. (1UYA and 1ETN are the experimentally defined 3D structures of UG and ST, respectively, which are known to possess high biological activity (36,37); the 3D structures were available in the Protein Data Bank.)

TABLE 1

The values of dihedral angles (in degrees) for peptide backbone in the "template" conformation of UG

| Residue | Angle | Conformer's # 1 | 3 | 9 | 22 | 25 | 27 |
|---|---|---|---|---|---|---|---|
| $Cys^4$ | ψ | −37 | −41 | −40 | −55 | −38 | −54 |
| $Glu^5$ | Φ | −71 | −67 | −72 | −69 | −68 | −70 |
| | Ψ | −50 | −47 | −48 | −33 | −43 | −22 |
| $Leu^6$ | Φ | −86 | −86 | −85 | −81 | −88 | −91 |
| | Ψ | 163 | 165 | 160 | 153 | 160 | 156 |
| $Cys^7$ | Φ | −79 | −82 | −79 | −83 | −79 | −81 |
| | Ψ | 74 | 68 | 78 | 67 | 75 | 72 |
| $Val^8$ | Φ | −120 | −114 | −126 | −124 | −125 | −128 |
| | Ψ | −65 | −57 | −62 | −55 | −60 | −64 |
| $Asn^9$ | Φ | −83 | −95 | −82 | −88 | −89 | −82 |
| | ψ | 119 | 113 | 134 | 118 | 111 | 116 |
| $Val^{10}$ | Φ | −84 | −82 | −97 | −90 | −82 | −82 |
| | Ψ | −21 | −13 | −16 | −4 | −15 | −16 |
| $Ala^{11}$ | Φ | −79 | −86 | −87 | −89 | −85 | −80 |
| | Ψ | −32 | −21 | −35 | −35 | −18 | −27 |
| $Cys^{12}$ | Φ | −86 | −92 | −78 | −79 | −95 | −90 |
| | Ψ | −52 | −53 | −55 | −57 | −53 | −54 |
| $Thr^{13}$ | Φ | −129 | −121 | −127 | −119 | −118 | −130 |
| | Ψ | 111 | 153 | 141 | 155 | 141 | 119 |
| $Gly^{14}$ | Φ | −64 | −78 | −78 | −80 | −78 | −68 |
| | Ψ | 83 | 64 | 68 | 62 | 67 | 78 |
| $Cys^{15}$ | Φ | −139 | −160 | −150 | −156 | −78 | −131 |

The dihedral angles Φ and ψ, values that determine the overall 3D shape of this UG fragment, are similar (Table 1). It allowed performing preliminary design of new analogs aimed at stabilizing this particular family of conformations employing the known local conformational limitations imposed by various types of amino acids.

For instance, it is known that Gly is more conformationally flexible compared to any other L-amino acid residue, since Gly may adopt conformations with any of the four combinations of signs for Φ and ψ, i.e., −, +; −,−; +,+; and +,−. The last combination is sterically forbidden for the L-amino acids, as Ala. Therefore, substitution of $Gly^{14}$ for $Ala^{14}$ should limit conformational flexibility in position 14 preserving the conformations described in Table 1. Also, substitution for Aib (α-Me-Ala, di-α-methyl-alanine) should limit the local conformational flexibility by two regions only, namely for −,− and +,+, the first one being compatible with conformers of $Ala^{11}$ in Table 1. Therefore, one more desirable substitution is $Aib^{11}$. In Pro, the Φ value is fixed at −75°; this residue is also similar to valine by its hydrophobic properties. Therefore, $Val^{10}$ may be replaced by $Pro^{10}$, which adds more local conformational constraints to the UG conformers in Table 1. Replacement by Pro also requires that the preceding residue possesses only positive ψ values; $Asn^9$ in Table 1 fulfills this requirement. The Pro residue already exists in the corresponding position of ST. All suggested substitutions within SEQ ID NO:1 shown below (e.g., $Pro^{10}$, $Aib^{11}$ or $Ala^{14}$) do not change the chemical nature of the non-aliphatic amino acids (such as Asn, Asp or Thr), which may be important for the actual interaction with receptor. The former substitutions should lead only to conformational limitations shifting conformational equilibrium in UG towards the suggested "template" 3-D shape.

Based on the 3D structures defined in Table 1, a three-dimensional pharmacophore for uroguanylin was defined, enabling the determination of distances between functional groups of uroguanylin thought to directly interact with the receptor. Those groups thought to directly interact with the receptor are side groups of residues in positions 3, 5, 9 and 13 of the backbone sequence. Preferably, the residues are Glu3, Glu5, Asn9, and Thr13, as shown in SEQ ID NO:2 and SEQ ID NO:20. Thus, a three dimensional pharmacophore of uroguanylin is described in which the spatial arrangement of the four side chains of the residues at positions 3, 5, 9 and 13 may be created such that the distances between these side chains enable optional biological activity. Those distances (measured as distances between C.beta. atoms of corresponding residues) are as follows: from 5.7 to 7.6 Å for the 3-5 distance, from 4.0 to 6.0 Å for 3-9; from 7.7 to 8.3 Å for 3-13, from 9.4 to 9.5 Å for 5-9, from 9.4 to 9.5 Å for 5-13, and from 5.8 to 6.3 Å for 9-13.

The distances above depend only on conformations of the peptide backbone. In some cases, however, conformations of side chains themselves are also important. For instance, calculations showed that there is no conformational difference between the backbones of UG (SP301), $[Glu^2]$-UG (SP303), $[Glu^3]$-UG (SP304) and $[Glu^2, Glu^3]$-UG (SP302) in terms of their low-energy conformations. However, there is a distinct difference in the spatial positions of the β-carboxyls of Asp and γ-carboxyls of Glu in position 3. Namely, γ-carboxyls of the Glu residues in position 3 are clearly stretched "outwards" of the bulk of the molecules farther than the corresponding β-carboxyls of the Asp residues. The above observation strongly suggests that the negatively charged carboxyl group of the side chain in position 3 specifically interacts with a positively charged binding site on the receptor; therefore, analogs containing $Glu^3$ instead of $Asp^3$ should be more active. At the same time, to ensure efficiency of this particular interaction, an entire system of the long-range electrostatic interactions between ligand and receptor should be well balanced. Since the $Glu^2$ side chain presents more conformational possibilities compared to the $Asp^2$ side chain, this balance may be slightly changed in SP302 (double substitution of Asp's for Glu's) compared to SP304 (single substitution of $Asp^3$ for $Glu^3$).

Compounds capable of adopting low-energy conformations described in Table 1 are listed in Table 2. All compounds are [4,12; 7,15] bicycles.

TABLE 2

1. Parent compound, uroguanylin
SEQ ID NO: 1
$Asn^1$-$Asp^2$-$Asp^3$-$Cys^4$-$Glu^5$-$Leu^6$-$Cys^7$-$Val^8$-$Asn^9$-$Val^{10}$-
$Ala^{11}$-$Cys^{12}$-$Thr^{13}$-$Gly^{14}$-$Cys^{15}$-$Leu^{16}$ 2. Compounds without modifications of cysteines:
Common sequence (SEQ ID NO: 2):
$Asn^1$-$Xaa^2$-$Xaa^3$-$Cys^4$-$Glu^5$-$Leu^6$-$Cys^7$-$Val^8$-$Asn^9$-$Xaa^{10}$-
$Xaa^{11}$-$Cys^{12}$-$Thr^{13}$-$Xaa^{14}$-$Cys^{15}$-$Leu^{16}$
where $Xaa^2$ = Asp, Glu; $Xaa^3$ = Asp, Glu with the exception that $Xaa^2$ and $Xaa^3$ are not both Asp TABLE 2-continued in same molecule
And where $Xaa^{10}$ = Val, Pro; $Xaa^{11}$ = Ala, Aib;
$Xaa^{14}$ = Gly, Ala 3. Compounds with mercaptoproline (Mpt) substituted for cysteine in position 7:
$Asn^{1}$-$Xaa^{2}$-$Xaa^{3}$-$Cys^{4}$-$Glu^{5}$-$Leu^{6}$-$Xaa^{7}$-$Val^{8}$-$Asn^{9}$-$Xaa^{10}$-
$Xaa^{11}$-$Cys^{12}$-$Thr^{13}$-$Xaa^{14}$-$Cys^{15}$-$Leu^{16}$
where $Xaa^{2}$ = Asp, Glu; $Xaa^{3}$ = Asp, Glu
where $Xaa^{10}$ = Val, Pro; $Xaa^{11}$ = Ala, Aib;
$Xaa^{14}$ = Gly, Ala 4. Compounds with penicillamines (β, β-dimethyl-cysteines, Pen) substituted for cysteines:
Common sequence (SEQ ID NO: 4):
$Asn^{1}$-$Xaa^{2}$-$Xaa^{3}$-$Xaa^{4}$-$Glu^{5}$-$Leu^{6}$-$Xaa^{7}$-$Val^{8}$-$Asn^{9}$-$Xaa^{10}$-
$Xaa^{11}$-$Xaa^{12}$-$Thr^{13}$-$Xaa^{14}$-$Xaa^{15}$-$Leu^{16}$
where $Xaa^{2}$ = Asp, Glu; $Xaa^{3}$ = Asp, Glu
where $Xaa^{10}$ = Val, Pro; $Xaa^{11}$ = Ala, Aib;
$Xaa^{14}$ = Gly, Ala and $Xaa^{4}$, $Xaa^{7}$, $Xaa^{12}$, $Xaa^{15}$ are either Cys or Pen (except not all are Cys in the same comformer)

5. Compounds with lactam bridges substituted for disulfide bridges:
Common sequence (SEQ ID NO: 5):
$Asn^{1}$-$Xaa^{2}$-$Xaa^{3}$-$Xaa^{4}$-$Glu^{5}$-$Leu^{6}$-$Xaa^{7}$-$Val^{8}$-$Asn^{9}$-$Xaa^{10}$-
$Xaa^{11}$-$Xaa^{12}$-$Thr^{13}$-$Xaa^{14}$-$Xaa^{15}$-$Leu^{16}$
where $Xaa^{2}$ = Asp, Glu; $Xaa^{3}$ = Asp, Glu
where $Xaa^{10}$ = Val, Pro; $Xaa^{11}$ = Ala, Aib;
$Xaa^{14}$ = Gly, Ala
and all combinations of the following (Dpr is diaminopropionic acid):
$Xaa^{4}$ is either Asp or Glu, and $Xaa^{12}$ is Dpr;
$Xaa^{7}$ is either Cys or Pen;
$Xaa^{5}$ is either Cys or Pen;
or:
$Xaa^{7}$ is Dpr and $Xaa^{15}$ is either Asp or Glu;
$Xaa^{7}$ is either Asp or Glu, and $Xaa^{15}$ is Dpr;
$Xaa^{4}$ is either Cys or Pen;
$Xaa^{12}$ is either Cys or Pen;

Some of the peptides shown in Table 2 contain 16 amino acid residues in which cysteine residues form disulfide bridges between $Cys^{4}$ and $Cys^{12}$, and $Cys^{7}$ and $Cys^{15}$, respectively. These peptides differ from the peptide sequences described in WO 01/25266, and are designed on the basis of peptide conformation and energy calculations.

In addition, peptides, varying in length from 13 to 16 amino acids, shown in Table 3, are designed, based on energy calculations and three-dimensional structures, to promote stabilization of the biologically active conformer and minimize or eliminate interconversion to biologically inactive conformers. These peptides are also designed to promote stability against proteolysis and higher temperatures. The design of these peptides involves modifications of amino acid residues that contain ionic charges at lower pH values, such as glutamic and aspartic acids.

TABLE 3

| | | | | | | | | | | | | | | | | |
|---|---|---|---|---|---|---|---|---|---|---|---|---|---|---|---|---|
| SEQ ID NO: 6 | X1 | Glu | Glu | Cys | X2 | X3 | Cys | X4 | Asn | X5 | X6 | Cys | X7 | X8 | Cys | X9 |
| SEQ ID NO: 7 | X1 | Glu | Asp | Cys | X2 | X3 | Cys | X4 | Asn | X5 | X6 | Cys | X7 | X8 | Cys | X9 |
| SEQ ID NO: 8 | X1 | Asp | Glu | Cys | X2 | X3 | Cys | X4 | Asn | X5 | X6 | Cys | X7 | X8 | Cys | X9 |
| SEQ ID NO: 9 | X1 | Asp | Asp | Cys | X2 | X3 | Cys | X4 | Tyr | X5 | X6 | Cys | X7 | X8 | Cys | X9 |
| SEQ ID NO: 10 | X1 | Glu | Glu | Cys | X2 | X3 | Cys | X4 | Tyr | X5 | X6 | Cys | X7 | X8 | Cys | X9 |
| SEQ ID NO: 11 | X1 | Asp | Glu | Cys | X2 | X3 | Cys | X4 | Tyr | X5 | X6 | Cys | X7 | X8 | Cys | X9 |
| SEQ ID NO: 12 | X1 | Glu | Asp | Cys | X2 | X3 | Cys | X4 | Tyr | X5 | X6 | Cys | X7 | X8 | Cys | X9 |
| SEQ ID NO: 13 | X1 | Asp | Asp | Cys | X2 | X3 | Cys | X4 | Gln | X5 | X6 | Cys | X7 | X8 | Cys | X9 |
| SEQ ID NO: 14 | X1 | Glu | Glu | Cys | X2 | X3 | Cys | X4 | Gln | X5 | X6 | Cys | X7 | X8 | Cys | X9 |
| SEQ ID NO: 15 | X1 | Asp | Glu | Cys | X2 | X3 | Cys | X4 | Gln | X5 | X6 | Cys | X7 | X8 | Cys | X9 |
| SEQ ID NO: 16 | X1 | Glu | Asp | Cys | X2 | X3 | Cys | X4 | Gln | X5 | X6 | Cys | X7 | X8 | Cys | X9 |
| SEQ ID NO: 17 | | | Glu | Cys | X2 | X3 | Cys | X4 | Asn | X5 | X6 | Cys | X7 | X8 | Cys | X9 |
| SEQ ID NO: 18 | | | Glu | Cys | X2 | X3 | Cys | X4 | Asn | X5 | X6 | Cys | X7 | X8 | Cys | |
| SEQ ID NO: 19 | | X1 | Glu | Cys | X2 | X3 | Cys | X4 | Asn | X5 | X6 | Cys | X7 | X8 | Cys | X9 |
| | 1 | 2 | 3 | 4 | 5 | 6 | 7 | 8 | 9 | 10 | 11 | 12 | 13 | 14 | 15 | 16 |
| SEQ ID NO: 20 | Asn | Asp | Glu | Cys | Glu | Leu | Cys | Val | Asn | Val | Ala | Cys | Thr | Gly | Cys | Leu |
| SEQ ID NO: 21 | | | Glu | Cys | Glu | Leu | Cys | Val | Asn | Val | Ala | Cys | Thr | Gly | Cys | Leu |

X1 to X9 can be any amino acid. The disulfide bridges are formed between Cys residues at 4 and 12 and between 7 and 15, respectively. SEQ ID NO:18 represents the minimum length requirement for these peptides to bind a guanylate cyclase receptor.

Pharmaceutical Compositions and Formulations

The guanylate cyclase receptor agonists of the present invention (Table 2; SEQ ID NOs:2-5 and Table 3; SEQ ID NOs:6-21), as well as uroguanylin, guanylin and/or bacterial enterotoxin ST, may be combined or formulated with various excipients, vehicles or adjuvants for oral, local or systemic administration. Peptide compositions may be administered in solutions, powders, suspensions, emulsions, tablets, capsules, transdermal patches, ointments, or other formulations. Formulations and dosage forms may be made using methods well known in the art (see, e.g., Remington's Pharmaceutical Sciences, 16$^{th}$ ed., A. Oslo ed., Easton, Pa. (1980)).

Inhibitors of cGMP-dependent phosphodiesterase may be small molecules, peptides, proteins or other compounds that specifically prevent the degradation of cGMP. Inhibitory compounds include suldinac sulfone, zaprinast, motapizone and other compounds that block the enzymatic activity of cGMP-specific phosphodiesterases. One or more of these compounds may be combined with a guanylate cyclase receptor agonist exemplified in SEQ ID NOs:2-21, uroguanylin, guanylin and *E. Coli* ST peptide.

The selection of carriers (e.g., phosphate-buffered saline or PBS) and other components suitable for use in compositions is well within the level of skill in this art. In addition to containing one or more guanylate cyclase receptor agonists, such compositions may incorporate pharmaceutically acceptable carriers and other ingredients known to facilitate administration and/or enhance uptake. Other formulations, such as microspheres, nanoparticles, liposomes, pegylated protein or peptide, and immunologically-based systems may also be used. Examples include formulations employing polymers (e.g., 20% w/v polyethylene glycol) or cellulose, or enteric formulations and pegylated peptide analogs for increasing systemic half-life and stability.

Treatment Methods

The term "treatment" refers to reducing or alleviating symptoms in a subject, preventing symptoms from worsening or progressing, or preventing disease development. For a given subject, improvement in a symptom, its worsening, regression, or progression may be determined by any objective or subjective measure typically employed by one of skill in the art. Efficacy of the treatment in the case of cancer may be measured as an improvement in morbidity or mortality (e.g., lengthening of the survival curve for a selected population). Thus, effective treatment would include therapy of existing disease, control of disease by slowing or stopping its progression, prevention of disease occurrence, reduction in the number or severity of symptoms, or a combination thereof. The effect may be shown in a controlled study using one or more statistically significant criteria.

Combination therapy with one or more medical/surgical procedures and/or at least one other chemotherapeutic agent may be practiced with the invention. Other suitable agents useful in combination therapy include anti-inflammatory drugs such as, for example, steroids or non-steroidal anti-inflammatory drugs (NSAIDS), such as aspirin and the like. Prophylactic methods for preventing or reducing the incidence of relapse are also considered treatment.

Cancers expected to be responsive to compositions include breast, colorectal, lung, ovarian, pancreatic, prostatic, renal, stomach, bladder, liver, esophageal and testicular carcinoma. Further examples of diseases involving cancerous or precancerous tissues that should be responsive to a therapeutic comprising at least one guanylate cyclase receptor agonist include: carcinoma (e.g., basal cell, basosquamous, Brown-Pearce, ductal, Ehrlich tumor, in situ, Krebs, Merkel cell, small or non-small cell lung, oat cell, papillary, bronchiolar, squamous cell, transitional cell, Walker), leukemia (e.g., B-cell, T-cell, HTLV, acute or chronic lymphocytic, mast cell, myeloid), histiocytoma, histiocytosis, Hodgkin disease, non-Hodgkin lymphoma, plasmacytoma, reticuloendotheliosis, adenoma, adeno-carcinoma, adenofibroma, adenolymphoma, ameloblastoma, angiokeratoma, angiolymphoid hyperplasia with eosinophilia, sclerosing angioma, angiomatosis, apudoma, branchioma, malignant carcinoid syndrome, carcinoid heart disease, carcinosarcoma, cementoma, cholangioma, cholesteatoma, chondrosarcoma, chondroblastoma, chondrosarcoma, chordoma, choristoma, craniopharyngioma, chrondroma, cylindroma, cystadenocarcinoma, cystadenoma, cystosarcoma phyllodes, dysgerminoma, ependymoma, Ewing sarcoma, fibroma, fibro-sarcoma, giant cell tumor, ganglioneuroma, glioblastoma, glomangioma, granulosa cell tumor, gynandroblastoma, hamartoma, hemangioendothelioma, hemangioma, hemangio-pericytoma, hemangiosarcoma, hepatoma, islet cell tumor, Kaposi sarcoma, leiomyoma, leiomyosarcoma, leukosarcoma, Leydig cell tumor, lipoma, liposarcoma, lymphangioma, lymphangiomyoma, lymphangiosarcoma, medulloblastoma, meningioma, mesenchymoma, mesonephroma, mesothelioma, myoblastoma, myoma, myosarcoma, myxoma, myxosarcoma, neurilemmoma, neuroma, neuroblastoma, neuroepithelioma, neurofibroma, neurofibromatosis, odontoma, osteoma, osteosarcoma, papilloma, paraganglioma, paraganglioma nonchromaffin, pinealoma, rhabdomyoma, rhabdomyosarcoma, Sertoli cell tumor, teratoma, theca cell tumor, and other diseases in which cells have become dysplastic, immortalized, or transformed.

A bolus of the inventive composition may be administered over a short time. Once a day is a convenient dosing schedule to treat, inter alia, one of the above-mentioned disease states. Alternatively, the effective daily dose may be divided into multiple doses for purposes of administration, for example, two to twelve doses per day. The dose level selected for use will depend on the bioavailability, activity, and stability of the compound, the route of administration, the severity of the disease being treated, and the condition of the subject in need of treatment. It is contemplated that a daily dosage will typically be between about 10 μg and about 2 mg (e.g., about 100 μg to 1 mg) of the compound per kilogram body weight. The amount of compound administered is dependent upon factors known to a person skilled in this art such as, for example, chemical properties of the compound, route of administration, location and type of cancer, and the like.

The subject mammal may be any animal or human patient. Thus, both veterinary and medical treatments are envisioned according to the invention.

The invention will be further described by the following non-limiting example.

EXAMPLES

Materials and Methods

Cell Culture: Human T84 colon carcinoma cells were obtained from the American Type Culture Collection at passage 52. Cells were grown in a 1:1 mixture of Ham's F-12 medium and Dulbecco's modified Eagle's medium (DMEM) supplemented with 10% fetal bovine serum, 100 U penicillin/ ml, and 100 μg/ml streptomycin. The cells were fed fresh medium every third day and split at a confluence of approximately 80%.

T84 cell-based assay for determining the intracellular levels of cGMP: Peptide analogs were custom synthesized by Multiple Peptide Systems, San Diego, Calif., and by Princeton Biomolecules, Langhorne, Pa. Biological activity of the synthetic peptides was assayed as previously reported (15). Briefly, the confluent monolayers of T-84 cells in 24-well plates were washed twice with 250 μl of DMEM containing 50 mM HEPES (pH 7.4), pre-incubated at 37° C. for 10 min with 250 μl of DMEM containing 50 mM HEPES (pH 7.4) and 1 mM isobutylmethylxanthine (IBMX), followed by incubation with peptide analogs (0.1 nM to 10 μM) for 30 min. The medium was aspirated, and the reaction was terminated by the addition of 3% perchloric acid. Following centrifugation, and neutralization with 0.1 N NaOH, the supernatant was used directly for measurements of cGMP using an ELISA kit (Caymen Chemical, Ann Arbor, Mich.).

Results

Peptides shown in Table 4 were custom synthesized and purified (>95% purity) using a published procedure (38). Peptide analogs were evaluated in the T84 cell-based assay for their ability to enhance intracellular levels of cGMP. As shown in Table 4, SP304 (SEQ ID NO:20) gave the greatest enhancement of intracellular cGMP of all the analogs tested. SP316 (SEQ ID NO:21) was second in effectiveness, whereas the biological activities of SP301, SP302 and SP303 were all somewhat weaker. The peptide analogs SP306 and SP310 were not active in this assay. These results indicate that SP304 is the most potent peptide for enhancing cGMP. These results also suggest that the cysteine residue at position 7 cannot be substituted with penicillamine as a component of the [7,15] disulfide linkage, and that the Asn residue at position 9 cannot be changed to a Gln.

TABLE 4

Peptide agonists evaluated for biological activity in the T84 cell bioassay.

| SEQ ID NO.* | Compound Code | cGMP Level** (pmol/well) |
|---|---|---|
| 1 | SP 301 | 205 |
| 6 | SP 302 | 225 |
| 7 | SP 303 | 195 |
| 20 | SP 304 | 315 |
| 14 | SP 306 | 0 |
| 4 | SP 310 | 0 |
| 21 | SP 316 | 275 |

*SEQ ID's for SP301, SP304 and SP316 are the precise amino acid sequences for these analogs as given in the text.

**Intracellular cGMP level observed in T84 cells following treatment with 1 micromolar solution of the respective peptide agonist for 30 minutes. The value observed for SP304 was statistically significant with a p > 0.5.

To examine heat stability, 10 micromolar solutions of peptide analogs were heated at 95° C. for up to 90 minutes. At specific times during the treatment, samples were tested for their biological activity in the T84 cell-based assay. Biological activity of SP301, SP302, SP303 and SP304 did not change significantly after 60 minutes of heating. After 90 minutes, the activities of SP301, SP302 and SP303 were reduced to about 80% of their original values, whereas the biological activity of SP304 remained unaltered. This indicates that SP304 is more stable to heat denaturation compared to the other peptides tested. Based on energy calculations and 3D structure, we expected that the negatively charged carboxyl group of the side chain in position 3 of SEQ ID NO:1 specifically interacts with a positively charged binding site on the receptor. In the case where this interaction can be enhanced, analogs containing $Glu^3$ instead of $Asp^3$ should be more active, as was found to be the case with SP304. At the same time, to ensure efficiency of this particular interaction, an entire system of the long-range electrostatic interactions between ligand and receptor should be well balanced. Since the $Glu^2$ side chain presents more conformational possibilities compared to the $Asp^2$ side chain, this balance may be slightly changed in SP302 (double substitution of Asp's for Glu's) compared to SP304 (single substitution of $Asp^3$ for $Glu^3$). Indeed, biological activity of SP 304 is the best amongst the analogs evaluated.

Synthetic peptides SP301, SP302, SP303 and SP304 were also tested for their activities at different pH values of the T84 cell-based assay. Whereas all of these peptides showed enhanced intracellular production of cGMP at pH's ranging from 5 to 7, SP304 showed the greatest enhancement in the range between 6.5 and 7. It is important to note that the physiological pH of the large intestine is in a similar range, and, therefore, SP304 would be expected to be especially efficacious for colon cancer treatment.

We also evaluated peptides used either alone or in combination with inhibitors of cGMP dependent phosphodiesterase (e.g., zaprinast or sulindac sulfone) in T84 cell-based assays for enhancement of intracellular levels of cGMP. Combinations of an inhibitor of cGMP dependent phosphodiesterase with SP304 displayed a dramatic effect in enhancing cGMP levels in these experiments. Synthetic peptide SP304 substantially increased the cGMP level over the level reached in the presence of either zaprinast or sulindac sulfone alone. Treatment of wells with SP304 in combination with either Zaprinast or sulindac sulfone resulted in synergistic increases in intracellular cGMP levels. These increases were statistically significant, with p values of <0.5. These data indicate that treatments combining a peptide agonist of a guanylate cyclase receptor with one or more inhibitors of cGMP dependent phosphodiesterase result in a greater than additive increase in cGMP concentrations.

While the invention has been described in detail and with reference to specific embodiments thereof, it will be apparent to those of ordinary skill in the art that various changes and modifications can be made without departing from the spirit and scope of the invention.

REFERENCES

1. Currie, et al., *Proc. Nat'l Acad. Sci. USA* 89:947-951 (1992).
2. Hamra, et al., *Proc. Nat'l Acad. Sci. USA* 90:10464-10468 (1993).
3. Forte, L., *Reg. Pept.* 81:25-39 (1999).
4. Schulz, et al., *Cell* 63:941-948 (1990).
5. Guba, et al., *Gastroenterology* 111:1558-1568 (1996).
6. Joo, et al., *Am. J. Physiol.* 274:G633-G644 (1998).
7. Evan, et al., *Nature* (London) 411:342-348 (2001). 8. Eastwood, G., J. Clin. Gastroenterol. 14:S29-33 (1992).
9. Lipkin, M. *Arch. Fr. Mal. Appl Dig.* 61:691-693 (1972).
10. Wong, et al., *Gut* 50:212-217 (2002).
11. Potten, et al., *Stem Cells* 15:82-93.
12. Basoglu, et al., in: *Proceedings of the Second FEPS Congress*, Jun. 29-Jul. 4, 1999, Prague, Czech Republic., http://f2.cuni.cz/physiolres/feps/basoglu.htm.
13. Sindic, et al., *J. Biol. Chem. Mar.* 11, 2002, manuscript M110627200 (in press).
14. Zhang, et al., *Science* 276:1268-1272 (1997).
15. Shailubhai, et al., *Cancer Res.* 60:5151-5157 (2000).

16. Shailubhai, et al., In: *Proceedings of the* 1999 *AACR.N-CI.EORTC International Conference*. November 1999, Abstract #0734.
17. Cohen, et al., *Lab. Invest.* 78:101-108 (1998).
18. Sciaky, et al., *Genomics* 26:427-429 (1995).
19. Whitaker, et al., *Genomics* 45:348-354 (1997).
20. Leister, et al., *Cancer Res.* 50:7232-7235 (1990).
21. Cheng, et al., *Cell* 63:827-834 (1990).
22. Welsh, et al., *Cell* 73:1251-1254 (1993).
23. Weber, et al., *Am. J. Physiol. Lung Cell Mol. Physiol.* 281(1):L71-78 (2001).
24. Venkatakrishnan, et al., *Am. J. Respir. Cell Mol. Biol.* 23(3):396-403 (2000).
25. Hudson, et al., *Free Radic. Biol. Med.* 30:1440-1461 (2001).
26. Bhakdi, et al., *Infect. Immun.* 57:3512-3519 (1989).
27. Hughes, et al, *J. Biol. Chem.* 272:30567-30576 (1997).
28. Cermak, et al., *Pflugers Arch.* 43:571-577 (1996).
29. Wu, et al., *J. Biol. Chem.* 272:14860-14866 (1997).
30. Nikiforovich, G., *Int. J. Pept. Prot. Res.* 44:513-531 (1994).
31. Dunfield, et al., *J. Phys. Chem.* 82:2609-2616 (1978).
32. Nemethy, et al., *J. Phys. Chem.* 87:1883-1887 (1983).
33. Zimmerman, et al., *Biopolymers* 16:811-843 (1977).
34. Nikiforovich, et al., *Biopolymers* 31:941-955 (1991).
35. Nyburg, S., *Acta Crystallographica* B30 (part 1):251-253 (1974).
36. Chino, et al., *FEBS Letters* 421:27-31 (1998).
37. Schulz, et al., *J. Peptide Res.* 52:518-525 (1998).
38. Klodt, et al., *J. Peptide Res.* 50:222-230 (1997).
39. Shailubhai, I., *Curr. Opin. Drug Discov. Devel.* 5:261-268 (2002)

---

What is claimed is:

1. A method for treating inflammatory bowel disease in a patient comprising administering to said patient an effective dosage of a peptide consisting of SEQ ID NO:8, wherein said peptide is a (4,12; 7,15) bicycle and wherein said peptide binds a guanylate cyclase receptor and induces cGMP production.

2. Themethod of claim 1, wherein said peptide consists of the sequence of SEQ ID NO:20.

3. The method of claim 1, wherein said inflammatory bowel disease is selected from the group consisting of ulcerative colitis and Crohn's disease.

4. The method of claim 1, further comprising administering to said patient an effective dose of an inhibitor of cGMP-dependent phosphodiesterase either concurrently or sequentially with said guanylate cyclase receptor agonist, wherein said inhibitor of cGMP-dependent phosphodiesterase is selected from the group consisting of sulindac sulfone, zaprinast, and motapizone.

* * * * *